United States Patent [19]

Sugimura et al.

[11] Patent Number: 5,633,243

[45] Date of Patent: May 27, 1997

[54] ANTI-TUMOR PLATINUM COMPLEXES, THEIR PREPARATION AND THEIR THERAPEUTIC USE

[75] Inventors: Yukio Sugimura; Tomoyuki Shibata; Yukiko Kameyama; Kimio Iino; Shigeki Muramatsu; Tomowo Kobayashi; Toshihiko Hashimoto, all of Tokyo, Japan

[73] Assignee: Sankyo Company, Limited, Tokyo, Japan

[21] Appl. No.: 472,128

[22] Filed: Jun. 7, 1995

Related U.S. Application Data

[62] Division of Ser. No. 341,702, Nov. 18, 1994, Pat. No. 5,527,905, which is a continuation of Ser. No. 148,174, Nov. 4, 1993, abandoned, which is a continuation of Ser. No. 908,827, Jul. 2, 1992, abandoned, which is a continuation of Ser. No. 782,895, Oct. 23, 1991, abandoned, which is a continuation of Ser. No. 597,117, Oct. 12, 1990, abandoned, which is a continuation of Ser. No. 485,864, Feb. 23, 1990, abandoned, which is a continuation of Ser. No. 189,524, May 3, 1988, abandoned.

[30] Foreign Application Priority Data

May 8, 1987 [JP] Japan ................................. 62-112181
May 13, 1987 [JP] Japan ................................. 62-114500

[51] Int. Cl.$^6$ .......................... A61K 31/555; C07F 15/00; C07D 205/08; C07D 207/277
[52] U.S. Cl. ............................................ 514/184; 540/201
[58] Field of Search .............................. 540/201; 514/184

[56] References Cited

U.S. PATENT DOCUMENTS 4,169,846 10/1979 Kidani et al. ............................ 548/301

FOREIGN PATENT DOCUMENTS 0214862 3/1987 European Pat. Off. .

OTHER PUBLICATIONS

Rosenberg et al, "Platinum Compounds", Nature, 222, 385–386 (1965).
Yoshinori Kidani et al, "Antitumor Activity of Platinum (II) Complexes of 1,2–Diaminocyclohexane Isomers", Gann, 71, 637–643 (1980).
Drugs of the Future, "Carboplatinum", 8, (6) 489–491 (1983).
Pazdur, "Proc. Am. Soc. Clin. Oncol." 3, p. 219 #C–856 (1984).
Martin, Cancer Research 46, 2189 (1986).
Estey, Cancer. Treat. Reports 70, pp. 1105–1115 (1986).
Zee–Cheng, Meth and Find Expl Clin Pharmacol 10 (1988), pp. 67–71 only.
Schilder, Cancer Res, 54, 709–717 (1994).
Prestayko, "Cisplatin" (AP, 1980) pp. 183–191.
Winogrud, "The Nude Mouse in Oncology Research" (CRC Press, 1991) pp. 305–316.
Kolata, N.Y. Times Jul. 26, 1994, p. C3.
Dermer, Biol. Technology, 12 Mar. 1994, p. 320.
Martin, Cancer. Treat. Reports, 68, p. 1317 (1984).

Primary Examiner—Mark L. Berch
Attorney, Agent, or Firm—Frishauf, Holtz, Goodman, Langer & Chick, P.C.

[57] ABSTRACT

Compounds of formula (I):

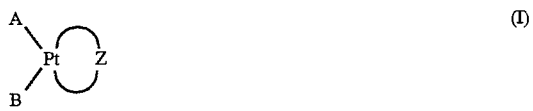

in which: A and B are separately monoamines or together diamines; and Z is a group of formula (II) or (III):

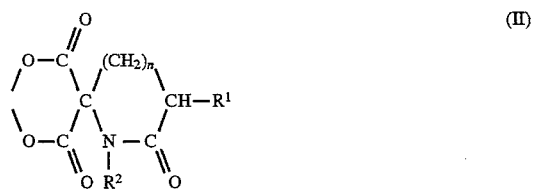

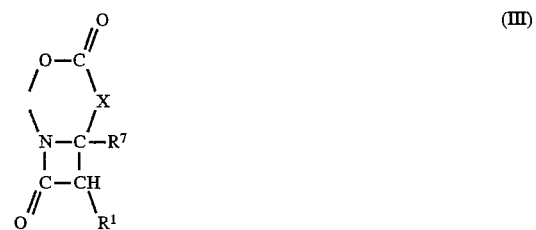

(in which $R^1$, $R^2$ and $R^7$ are various organic groups, n is 0, 1 or 2 and X is a direct carbon-carbon bond or lower alkylene) show valuable anti-tumor activity and may be prepared by reacting an amine-platinum complex with a compound providing the group represented by Z.

11 Claims, No Drawings

ANTI-TUMOR PLATINUM COMPLEXES, THEIR PREPARATION AND THEIR THERAPEUTIC USE

This is a division of application Ser. No. 08/341,702, filed Nov. 18, 1994, U.S. Pat. No. 5,527,905, which is a continuation of Ser. No. 08/148,174, filed Nov. 4, 1993, abandoned, which is a continuation of Ser. No. 07/908,827, filed Jul. 2, 1992 (abandoned), which is a continuation of application Ser. No. 07/782,895, filed Oct. 23, 1991 (abandoned), which is a continuation of application Ser. No. 07/597,117 filed Oct. 12, 1990 (abandoned), which is a continuation of application Ser. No. 07/485,864 filed Feb. 23, 1990 (abandoned), which is a continuation of application Ser. No. 07/189,524, filed May 3, 1988 (abandoned).

BACKGROUND TO THE INVENTION

The present invention relates to a series of novel complexes of quadricoordinate, divalent platinum with certain specified amino compounds. Such complexes have valuable anti-tumor activity with better solubility than known anti-tumor platinum compounds and complexes. The invention also provides a process for preparing these complexes and methods and compositions using them.

Cancerous disorders are a major medical problem but are often difficult to cure. The main reason for this is that the differences between tumor cells and normal cells are generally extremely small, with the result that compounds which are toxic to tumor cells are also toxic to normal cells. The chemotherapy of cancerous disorders is therefore generally dependent upon very limited differences between the susceptibilities of tumor cells and of normal cells to anti-tumor agents.

Various platinum compounds are known to have anti-tumor activities. For example cisplatin [Rosenberg et al, Nature 222, 385 (1965) and The Merck Index, tenth edition (1983) monograph 2289] has been successfully used in the treatment-of tumors, and malonato-(1,2-diaminocyclohexane)platinum(II) [e.g. U.S. Pat. No. 4,169, 846 and Kidani et al, Gann, 71, 637–643 (1980)] has also been proposed for such use. Both of the above platinum complexes have some structural similarity to the compounds of the invention. Another platinum complex, although structurally less similar to the compounds of the invention, which has recently become available for the treatment of tumors is carboplatin [Drugs of the Future, Vol. 8, No. 6, 489–491 (1983)]. However, most of the known platinum complexes, including those referred to above, have a high renal toxicity and a poor solubility in water, which makes it difficult to formulate them into an appropriate dosage form.

Another series of platinum complexes with a limited structural resemblance to the compounds of the present invention are disclosed in U.S. patent application Ser. No. 902,420, filed 29 Aug. 1986.

We have now discovered a novel series of platinum complexes which have good anti-tumor activity but relatively few side effects, such as renal toxicity and bone marrow suppression, and which have a good solubility in water.

BRIEF SUMMARY OF INVENTION

The compounds of the present invention are quadricoordinate, divalent platinum complexes, said complexes being represented by the formula (I):

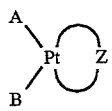

in which:

A and B are independently selected from the group consisting of ammine groups, $C_1$–$C_4$ alkylamine groups, dialkylamine groups in which each alkyl part is $C_1$–$C_4$ and arylamine groups in which the aryl part is a $C_6$–$C_{10}$ carbocyclic aromatic group which is unsubstituted or has at least one substituent selected from the group consisting of $C_1$–$C_4$ alkyl groups; or A and B together represent a compound of formula $H_2N$—Y—$NH_2$, where Y represents a $C_2$–$C_7$ alkylene group, a $C_6$–$C_{10}$ aromatic compound, a heterocyclic compound having from 5 to 8 ring atoms of which 1 or 2 are hetero-atoms selected from the group consisting of 0 or 1 nitrogen hetero-atoms and 0, 1 or 2 oxygen or sulfur hetero-atoms or an alicyclic compound having from 5 to 8 ring atoms in a single ring, in a bridged ring or in two fused rings, wherein said aromatic compound, said heterocyclic compound having 0 nitrogen hetero-atoms and said alicyclic compound have two substituents selected from the group consisting of amino groups and $C_1$–$C_4$ aminoalkyl groups and wherein said heterocyclic compound having 1 nitrogen hetero-atom has one substituent selected from the group consisting of amino groups and $C_1$–$C_4$ aminoalkyl groups;

and Z represents a group of formula (II):

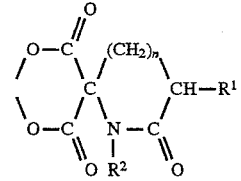

or a group of formula (III):

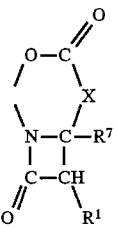

wherein:

$R^1$ represents a hydrogen atom, a $C_1$–$C_4$ alkyl group, a substituted $C_1$–$C_4$ alkyl group having at least one substituent selected from the group consisting of substituents (a), a $C_6$–$C_{10}$ carbocyclic aryl group, a $C_1$–$C_4$ alkyl group having at least one $C_6$–$C_{10}$ carbocyclic aryl substituent, a heterocyclic group having from 5 to 10 ring atoms of which in total from 1 to 4 are hetero-atoms selected from the group consisting of 0, 1, 2, 3 or 4 nitrogen atoms and 0, 1 or 2 oxygen or sulfur atoms, a $C_2$–$C_4$ aliphatic carboxylic acylamino group, a $C_7$–$C_{11}$ aromatic carboxylic acylamino group, a $C_2$–$C_4$ aliphatic carboxylic acylamino group having at least one $C_6$–$C_{10}$ carbocyclic aryl substituent, a $C_2$–$C_6$ alkoxycarbonyl group, a $C_1$–$C_4$ alkoxy group, a $C_1$–$C_4$ alkylthio group, a halogen atom, a cyano group or a phthalimido group, said heterocyclic groups and said $C_6$–$C_{10}$ carbocyclic aryl groups and substituents being unsubstituted or having at least one substituent selected from the group consisting of substituents (b);

$R^2$ represents a hydrogen atom, a $C_1$–$C_4$ alkyl group, a substituted $C_1$–$C_4$ alkyl group having at least one substituent selected from the group consisting of substituents (c), a $C_6$–$C_{10}$ carbocyclic aryl group, a $C_1$–$C_4$ alkyl group having at least one $C_6$–$C_{10}$ carbocyclic aryl substituent, said $C_6$–$C_{10}$ carbocyclic aryl groups and substituents being unsubstituted or having at least one substituent selected from the group consisting of substituents (c);

$R^7$ represents a hydrogen atom, a $C_1$–$C_4$ alkyl group, a substituted $C_1$–$C_4$ alkyl group having at least one substituent selected from the group consisting of substituents (c), a $C_2$–$C_6$ alkoxycarbonyl group or a cyano group;

X represents a single carbon-carbon bond or a $C_1$–$C_3$ alkylene group;

n is 0, 1 or 2;

substituents (a) are selected from the group consisting of hydroxy groups, silyloxy groups having from 1 to 3 substituents on the silicon atom selected from the group consisting of $C_1$–$C_4$ alkyl groups and $C_6$–$C_{10}$ carbocyclic aryl groups which are unsubstituted or have at least one substituent selected from the group consisting of substituents (b), $C_1$–$C_4$ alkoxy groups, halogen atoms, groups of formula —OPO($OR_3$)$_2$, —OSO$_2$$R^3$ and —O—COR$^4$, $C_2$–$C_5$ alkoxyalkoxy groups and $C_3$–$C_7$ alkoxyalkoxyalkoxy groups;

wherein:

$R^3$ represents a $C_1$–$C_4$ alkyl group, a $C_6$–$C_{10}$ carbocyclic aryl group or a $C_6$–$C_{10}$ carbocyclic aryl group having at least one substituent selected from the group consisting of substituents (b) and (c), and $R^4$ represents a $C_1$–$C_9$ alkyl group, a $C_2$–$C_5$ alkoxyalkyl group, a phenoxyalkyl group in which the alkyl part is $C_1$–$C_4$, an aralkyl group in which the alkyl part is $C_1$–$C_4$ and the aryl part is a $C_6$–$C_{10}$ carbocyclic aryl group which is unsubstituted or has at least one substituent selected from the group consisting of substituents (b) and (c), a $C_6$–$C_{10}$ carbocyclic aryl group which is unsubstituted or has at least one substituent selected from the group consisting of substituents (b) and (c), or a heterocyclic group having 5 or 6 ring atoms of which 1 or 2 are hetero-atoms selected from the group consisting of oxygen, sulfur and nitrogen hetero-atoms, said heterocyclic groups being unsubstituted or having at least one substituent selected from the group consisting of substituents (b) and substituents (b) are selected from the group consisting of hydroxy groups, $C_1$–$C_4$ alkyl groups, $C_1$–$C_4$ alkoxy groups and halogen atoms: and substituents (c) are selected from the group consisting of $C_1$–$C_4$ alkyl groups, $C_1$–$C_4$ alkoxy groups, $C_1$–$C_4$ alkylthio groups, $C_2$–$C_5$ alkoxyalkoxy groups and halogen atoms;

PROVIDED THAT substituents (b) and (c) are not said alkyl groups when they are substituents on alkyl groups.

The invention further provides a composition comprising an anti-tumor agent and a pharmaceutically acceptable carrier or diluent, wherein the anti-tumor agent is selected from the group consisting of compounds of formula (I).

The invention still further provides a method for the treatment of an animal, preferably a mammal (including human beings) suffering from a tumor, which comprises administering to said animal an effective amount of an anti-tumor agent, wherein the anti-tumor agent is selected from the group consisting of compounds of formula (I).

The invention still further provides methods of preparing the compounds of the present invention, as described in more detail hereafter.

DETAILED DESCRIPTION OF INVENTION

The compounds of the present invention contain a quadricoordinate, divalent platinum atom, two of whose coordinate positions are occupied by amino groups derived from one diamino or two monoamino compounds (represented by A and B) and the other two of whose coordinate positions are occupied by a carboxy oxygen atom and an amino nitrogen atom or by two carboxy oxygen atoms.

Where A and/or B represents a primary alkylamine, the alkyl part thereof has from 1 to 4 carbon atoms and examples of such compounds include methylamine, ethylamine, propylamine, isopropylamine, butylamine, sec-butylamine and t-butylamine. Where A and/or B represents a secondary alkylamine, each alkyl part contains from 1 to 4 carbon atoms, more preferably from 1 to 3 carbon atoms, and the two alkyl groups may be the same or different, but are preferably the same. Examples of such compounds include dimethylamine, diethylamine, dipropylamine, diisopropylamine, methylethylamine and methylpropylamine.

Where A and/or B represents an aromatic amine, the aromatic part is a carbocyclic aryl group having from 6 to 10 ring atoms and is preferably a phenyl or naphthyl (1- or 2-naphthyl) group. Such aryl groups may be unsubstituted or they may be substituted and, if substituted, the substituent(s) is or are selected from the group consisting of $C_1$–$C_4$ alkyl groups. There is, in principle, no limitation on the number of such substituents, the number being only limited by the number of substitutable positions and, possibly, by steric considerations; in general from 1 to 3 substituents are preferred, a single substituent being most preferred in this case. Examples of such aromatic amines include aniline, the toluidines (especially p-toluidine) and α- or β-naphylamine, of which aniline and p-toluidine are preferred, As an alternative, A and B together may represent a diamino compound, as defined above. For example, where A and B together represent a compound of formula $H_2N$—Y—$NH_2$, Y represents a $C_2$–$C_7$ alkylene group, which may be a straight or branched chain group. The two "free" valencies of the alkylene group may be attached to the same carbon atom (in which case such groups are sometimes referred to as "alkylidene" groups) or, and more preferably, they may be attached to different carbon atoms. Examples of such diamino compounds include ethylene diamine, trimethylene diamine (1,3-diaminopropane), 2-methyltetramethylene diamine (1,4-diamino-2-methylbutane) and 2,2-diethyltrimethylene diamine (1,3-diamino-2,2-diethylpropane).

An alternative class of diamines which may be represented by A and B are $C_5$–$C_8$ alicyclic diamines in which each amino group is provided by an amino substituent on the alicyclic ring or by a $C_1$–$C_4$ aminoalkyl substituent on the alicyclic ring; if desired, the compound may contain two such amino substituents, two such aminoalkyl substituents or one such amino substituent and one such aminoalkyl substituent. In the case of the aminoalkyl substituents, the alkyl part has from 1 to 4 carbon atoms, more preferably 1 or 2 carbon atoms and most preferably 1 carbon atom. Examples of such aminoalkyl groups include the aminomethyl, 2-aminoethyl, 3-aminopropyl and 4-aminobutyl groups, of which the aminomethyl group is preferred. The alicyclic ring system itself is preferably a cycloalkyl ring and may be a single, optionally bridged, ring or it may be provided by two fused rings, the total number of carbon atoms in the ring or rings being from 5 to 8.

Examples of such ring systems include the cyclopentane, cyclohexane, cycloheptane, cyclooctane, bicyclo[2.1.1] hexane, 8,9,10-trinorcarane, 8,9,10-trinorpinane and 8,9,10-trinorbornane systems, of which the cyclopentane, cyclohexane, cycloheptane, cyclooctane and bicyclo[2.1.1] hexane systems are preferred. Examples of particularly preferred such diamines include 1,1-bis[aminomethyl] cyclohexane, 1,2-diaminocyclopentane, 1-amino-2-aminomethylcyclopentane, 1,2-diaminocyclohexane, 1-amino-2-aminomethylcyclohexane, 1,2-diaminocycloheptane, 1,2-diaminocyclooctane and 2,3-diaminobicyclo[2.1.1]cyclohexane.

Another series of diamines which may be represented by A and B together are the aromatic diamines, in which the amino groups may, as with the alicyclic diamines, be provided by an amino substituent directly on the aromatic ring and/or by an aminoalkyl substituent in which the alkyl part has from 1 to 4 carbon atoms. Examples of such aminoalkyl substituents are as given above in relation to the alicyclic diamines. As with the alicyclic diamines, the compound may contain two amino groups directly attached to the aromatic ring, two aminoalkyl groups or one amino group attached to the aromatic ring and one aminoalkyl group. In this case, the preferred option is two amine groups attached directly to the aromatic ring. The aromatic ring is a $C_6$–$C_{10}$ ring, more preferably a $C_6$ or $C_{10}$ ring, i.e. benzene or napthalene. Examples of such aromatic diamines include m-phenylenediamine, 2,3-naphthylenediamine, 1-amino-2-aminomethylbenzene and 1,2-bis(aminomethyl)benzene.

As a further alternative, the diamine may be a compound in which one of the amine groups is provided by a nitrogen hetero-atom in a heterocyclic compound having the nitrogen atom as one hetero-atom and optionally having an oxygen atom as another hetero-atom. The heterocyclic ring may be aromatic or non-aromatic in character and contains, in total, 5 or 6 ring atoms. The other amine group is provided by an amine or aminoalkyl, preferably aminoalkyl, substituent on the heterocyclic ring, the alkyl part of which contains from 1 to 4 carbon atoms and examples of which are as given in relation to alicyclic diamines. Examples of such heterocyclic ring systems include pyrrole, isoxazole, pyridine, pyrrolidine, pyrroline, piperidine and morpholine. Specific examples of preferred such diamines include 2-aminomethylpyrrolidine, 3-aminomethylmorpholine, 2-aminomethylpiperidine and 2-aminomethylpyridine.

Another class of heterocyclic diamines are those in which the heterocyclic ring contains one or two oxygen or sulfur hetero-atoms but no nitrogen hetero-atoms and hence the two amine groups have to be provided by substituents on the heterocyclic ring. As with the alicyclic diamines, the compound may contain two amine groups directly attached to the heterocyclic ring, two aminoalkyl groups or one amine group attached to the heterocyclic ring and one aminoalkyl group. Examples of such heterocyclic rings include the thiophene, furan, pyran, 1,3-dioxane and 1,3-dithiane ring systems. Specific examples of such compounds include those corresponding to the alicyclic diamines exemplified above, but in which the alicyclic ring is replaced by one of the aforementioned heterocyclic rings. The most preferred of this class of heterocyclic diamines is 5,5-bis(aminomethyl)-1,3-dioxane.

Compounds of the present invention in which Z represents a group of formula (II) may be represented by the formula (Ia):

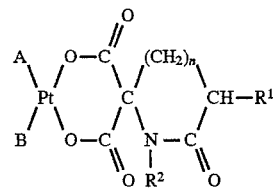

(in which A, B, $R^1$, $R^2$ and n are as defined above) and similarly those compounds of formula (I) in which Z represents a group of formula (III) may be represented by the formula (Ib):

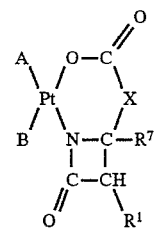

(in which A, B, $R^1$, $R^7$ and X are as defined above).

In the compounds of the invention, where $R^1$, $R^2$, $R^3$, $R^4$, $R^7$ substituent (b) or substituent (c) represents a $C_1$–$C_4$ alkyl group, this may be a straight or branched chain group and examples include the methyl, ethyl, propyl, isopropyl, butyl, sec-butyl and t-butyl groups. In the case of $R^1$, such an alkyl group may be unsubstituted or may have at least one substituent selected from the group consisting of substituents (a), as defined above, and as exemplified in greater detail hereafter. In the case of the alkyl groups represented by $R^2$ and $R^7$, these may be unsubstituted or may have one or more substituents selected from the group consisting of substituents (c), as defined above, and as exemplified in greater detail hereafter.

Where $R^1$, $R^2$, $R^3$ or $R^4$ represents an aryl group, this is a carbocyclic aryl group having from 6 to 10, and preferably 6 or 10, ring atoms, for example a phenyl or naphthyl (1- or 2-naphthyl) group. Such groups may be unsubstituted or may have one or more substituents selected from the group consisting of substituents (b), in the case of $R^1$, or substituents (c), in the case of $R^2$; in the case of $R^3$ and $R^4$, the aryl group represented by these symbols may be unsubstituted or have at least one substituent selected from the group consisting of substituents (b) and (c).

Where $R^1$, $R^2$ or $R^4$ represents an aralkyl group, the aryl part is a $C_6$–$C_{10}$ carbocyclic aryl group (which may be unsubstituted or have one or more substituents as defined above in relation to the aryl groups represented by the corresponding symbol) and the alkyl part is a $C_1$–$C_4$ alkyl group, e.g. as exemplified above in relation to $R^1$. The alkyl group more preferably has from 1 to 3, still more preferably 1 or 2 and most preferably 1, carbon atoms. Examples of such aralkyl groups include the benzyl, phenethyl, 1-phenylethyl, 2-phenylpropyl, 3-phenylpropyl, 4-phenylbutyl and benzhydryl groups. Such groups may be unsubstituted or substituted as defined above.

Where $R^1$ represents a heterocyclic group, this contains from 5 to 10 ring atoms, of which from 1 to 4, in total, are hetero-atoms selected from the group consisting of nitrogen, oxygen and sulfur atoms. In the case of nitrogen atoms, there may be up to 4 such hetero-atoms, whereas, in the case of oxygen and sulfur atoms, there may be up to 2 such atoms. The heterocyclic groups may be saturated ring systems or they may be unsaturated: we prefer those that are fully unsaturated. Examples of such heterocyclic groups include the furyl, thienyl, tetrazolyl, dioxanyl, pyranyl, chromenyl, pyrrolyl, imidazolyl, thiazolyl, isothiazolyl, oxazolyl, isoxazolyl, pyridyl, pyrazinyl, pyrimidinyl, pyridazinyl, indolizinyl, indolyl, isoindolyl, purinyl, quinolyl, isoquinolyl, cinnolinyl, furazanyl, chromanyl, pyrrolidinyl, pyrrolinyl, imidazolidinyl, imidazolinyl, pyrazolidinyl, pyrazolinyl, piperidyl, piperazinyl, indolinyl, isoindolinyl and morpholinyl groups, of which the furyl, thienyl and tetrazolyl groups are preferred. Such groups may be unsubstituted or they may have one or more substituents; if substituted, the substituents are selected from the group consisting of substituents (b), as defined above and as exemplified in greater detail below.

Where $R^1$ represents an aliphatic acylamino group, the acyl part as a carbocylic acyl group, which may be a straight or branched chain group, having up to 4 carbon atoms. The acylamino groups are preferably alkanoylamino groups, and examples of such groups include the acetamido, propionamido, butyramido and isobutyramido groups, of which the acetamido group is preferred. Such groups may be unsubstituted or may have one or more, preferably one, substituents selected from the group consisting of $C_6$–$C_{10}$ carbocyclic aryl groups, which may themselves be substituted or unsubstituted and, if substituted, may have one or more substituents selected from the group consisting of substituents (b) and (c), as defined above and exemplified below; however, the aryl groups in this case are preferably unsubstituted. Examples of such aryl-substituted acylamino groups include the phenylacetamido, 3-phenylpropionamido, 4-phenylbutyramido and α-naphthylacetamido groups, of which the phenylacetamido group is preferred.

Where $R^1$ represents an aromatic acylamino group, the aromatic part is a $C_6$–$C_{10}$ carbocyclic aryl group, which may be substituted or unsubstituted and, if substituted, preferably has one or more substituents selected from the group consisting of substituents (b) and (c). The acylamino group may be derived from monocarboxylic or dicarboxylic acids and examples of such groups include the benzamido, toluamido, α-naphthoylamino, β-naphthoylamino and phthalimido groups, of which the phthalimido group is preferred.

Where $R^1$ represents an alkoxycarbonyl group, this contains from 2 to 6 carbon atoms in total and may be a straight or branched chain group. Examples of such groups include the methoxycarbonyl, ethoxycarbonyl, propoxycarbonyl, isopropoxycarbonyl, butoxycarbonyl, sec-butoxycarbonyl, t-butoxycarbonyl and pentyloxycarbonyl groups, of which the methoxycarbonyl, ethoxycarbonyl, butoxycarhonyl and t-butoxycarbonyl groups are preferred.

Where $R^1$ represents an alkoxy group, this contains from 1 to 4 carbon atoms and may be a straight or branched chain group. Examples of such groups include the methoxy, ethoxy, propoxy, isopropoxy, butoxy, sec-butoxy and t-butoxy groups, of which the methoxy, ethoxy and propoxy groups are preferred.

Where $R^1$ represents an alkylthio group, this contains from 1 to 4 carbon atoms and may be a straight or branched chain group. Examples include the methylthio, ethylthio, propylthio, isopropylthio, butylthio, sec-butylthio and t-butylthio groups of which the methylthio and ethylthio groups are preferred.

Where $R^1$ represents a halogen atom, this may be a fluorine, chlorine, bromine or iodine atom, preferably a fluorine, chlorine or bromine atom.

Where $R^2$ represents ah alkyl group, this may be as exemplified above in relation to the alkyl groups which may be represented by $R^1$ etc., but is preferably a methyl, ethyl, propyl or isopropyl group. Such a group may be substituted or unsubstituted, and, if substituted, the substituents are preferably selected from the group consisting of substituents (c), as defined above and as exemplified hereafter, but are most preferably alkoxyalkyl or alkoxyalkoxyalkyl groups. Examples of such substituted groups include the methoxymethyl and methoxyethoxymethyl (especially 2-methoxyethoxymethyl) groups.

Where $R^2$ represents a $C_6$–$C_{10}$ carbocyclic aryl group, this is preferably a phenyl or naphthyl (e.g. 1- or 2-naphthyl) group, which may be substituted or unsubstituted, and, if substituted, may have one or more substituents selected from the group consisting of substituents (c), as defined above and exemplified below.

Where $R^2$ represents a $C_1$–$C_4$ alkyl group having at least one aryl substituent, the aryl part may be as defined and exemplified above, and the alkyl part, which may be a straight or branched chain alkyl group, is preferably a methyl, ethyl or propyl group. Examples of the resulting aralkyl groups include the benzyl, phenethyl, 1-phenylethyl, 1-phenylpropyl, 2-phenylpropyl, 3-phenylpropyl, benzhydryl, α-naphthylmethyl and β-naphthylmethyl groups, of which the benzyl group is most preferred.

Where $R^7$ represents an alkyl group, this may be substituted or unsubstituted, and may be as defined and exemplified in relation to $R^2$, above.

Where $R^7$ represents an alkoxycarbonyl group, this has in total from 2 to 6 carbon atoms including the carbon atom of the carbonyl group, i.e. the alkoxy part has from 1 to 5 carbon atoms. This may be a straight or branched chain group, and examples include the methoxycarbonyl, ethoxycarbonyl, propoxycarbonyl, isopropoxycarbonyl, butoxycarbonyl and t-butoxycarbonyl groups, of which the ethoxycarbonyl group is preferred.

Where X represents a $C_1$–$C_3$ alkylene group, this may be a straight or branched chain group, and the two "free" valencies may be on the same carbon atom (in which case, the group is sometimes referred to as an "alkylidene" group) or on different carbon atoms. Examples of such alkylene groups include the methylene, ethylene, ethylidene [—CH(CH$_3$)—], isopropylidene [—C(CH$_3$)$_2$—] and trimethylene groups, of which the methylene, ethylidene and isopropylidene groups are preferred. However, X is more preferably a direct carbon-carbon bond or a methylene group.

In the compounds of the present invention where Z represents said group of formula (II), i.e. the compounds of formula (Ia), n may be 0, 1 or 2, but is preferably 0, i.e. the compounds are azetidene derivatives.

Where substituent (a) is a silyloxy group, this has from 1 to 3, preferably 3, substituents selected from the group consisting of $C_1$–$C_4$ alkyl groups (e.g. as exemplified above in relation to $R^1$) and $C_6$–$C_{10}$ aryl groups (e.g. as exemplified above in relation to $R^1$). Specific examples of preferred such silyloxy groups include the dimethyl-t-butylsilyloxy, trimethylsilyloxy, triethylsilyloxy, dimethyl(phenyl)silyloxy, methyl(diphenyl)silyloxy and triphenylsilyloxy groups, of which the dimethyl-t-butylsilyloxy and trimethylsilyloxy groups are preferred.

Where substituent (a) is an alkoxy group, this has from 1 to 4 carbon atoms and may be a straight or branched chain group. Examples include the methoxy, ethoxy, propoxy, isopropoxy, butoxy, sec-butoxy and t-butoxy groups, of which the methoxy, ethoxy and propoxy groups are preferred.

Where substituent (a) is a halogen atom, this is preferably a fluorine, chlorine, bromine or iodine atom, preferably a fluorine, chlorine or bromine atom.

Where substituent (a) is a group of formula —OPO(OR$_3$)$_2$, R$^3$ may be:

an alkyl group, e.g. as defined and exemplified in relation to R$^1$;

or an aryl group, which may be unsubstituted or have at least one substituent selected from the group consisting of substituents (b) and (c), e.g. as defined and exemplified in relation to R$^1$;

Most preferably, in this formula, R$^3$ represents a methyl, ethyl, propyl, phenyl or tolyl group.

Where substituent (a) represents a group of formula —OSO$_2$R$^3$, R$^3$ may be as defined above.

Where substituent (a) represents a group of formula —O—COR$^4$, R$^4$ may represent:

a C$_1$–C$_9$ alkyl group, e.g. a methyl, ethyl, propyl, isopropyl, butyl, sec-butyl, t-butyl, pentyl, isopentyl, hexyl, heptyl, octyl or nonyl group, of which the C$_1$–C$_7$ groups are the more preferred alkyl groups, the C$_7$ group being most preferred;

a C$_2$–C$_5$ alkoxyalkyl group, e.g. a methoxymethyl, ethoxymethyl, propoxymethyl, isopropoxymethyl, butoxymethyl, t-butoxymethyl, 2-methoxyethyl, 1-methoxyethyl, 2-ethoxyethyl, 2-propoxyethyl, 2-isopropoxyethyl, 3-methoxypropyl, 3-ethoxypropyl, 2-methoxy-1-methylethyl or 2-ethoxy-1-methylethyl group;

a phenoxyalkyl group in which the alkyl part is C$_1$–C$_4$, e.g. a phenoxymethyl, 2-phenoxyethyl, 3-phenoxypropyl, 4-phenoxybutyl, 1-phenoxyethyl, 2-phenoxy-1-methylethyl or 3-phenoxy-2-methylpropyl group;

an aralkyl group in which the alkyl part is C$_1$–C$_4$ and the aryl part is a C$_6$–C$_{10}$ carbocyclic aryl group which is unsubstituted or has at least one substituent selected from the group consisting of substituents (b) and (c), e.g. as exemplified above in relation to R$^2$;

a C$_6$–C$_{10}$ carbocyclic aryl group which is unsubstituted or has at least one substituent selected from the group consisting of substituents (b) and (c), e.g. as exemplified above in relation to R$^2$;

or a heterocyclic group having 5 or 6 ring atoms of which 1 or 2 are hetero-atoms selected from the group consisting of oxygen, sulfur and nitrogen hetero-atoms, said heterocyclic groups being unsubstituted or having at least one substituent selected from the group consisting of substituents (b) and (c), e.g. a furyl, thienyl, tetrazolyl, dioxanyl, pyranyl, pyrrolyl, imidazolyl, thiazolyl, isothiazolyl, oxazolyl, isoxazolyl, pyridyl, pyrazinyl, pyrimidinyl, pyridazinyl, pyrrolidinyl, pyrrolinyl, imidazolidinyl, imidazolinyl, pyrazolidinyl, pyrazolinyl, piperidyl, piperazinyl and morpholinyl groups, of which the furyl, thienyl and tetrazolyl groups are preferred and the furyl and thienyl groups are most preferred.

Where substituent (b) or (c) represents an alkyl or alkoxy group or a halogen atom, this may be as defined and exemplified above in relation to R$^1$. Where substituent (c) represents an alkylthio group, this may be as defined and exemplified above in relation to R$^1$. Where substituent (c) represents an alkoxyalkoxy group, this may be as defined and exemplified above in relation to substituents (a).

Examples of preferred compounds which may be represented by A and/or B include ammonia, isopropylamine, ethylenediamine, trimethylenediamine, 2-methyltetramethylenediamine, 2,2-diethylpropylene-1,3-diamine, 1,2-diaminocyclohexane, 1,2-diaminocycloheptane, 1,2-diaminocyclooctane, 1-amino-2-aminomethylcyclohexane, 1,1-bis(aminomethyl) cyclohexane, 5,5-bis(aminomethyl)-1,3-dioxane, 2-aminomethylpyrrolidine and 2-aminomethylpyridine.

Examples of preferred groups which may be represented by R$^1$ include the hydrogen, bromine and chlorine atoms and the methyl, ethyl, isopropyl, phenyl, benzyl, methoxymethyl, 1-hydroxyethyl, 1-trimethylsilyloxyethyl, 1-(t-butyldimethylsilyloxy)ethyl, 1-(dimethylphosphonoxy) ethyl, 1-(diethylphosphonoxy)ethyl, 1-(diphenylphosphonoxy)ethyl, 1-methoxyethyl, 1-methoxymethoxyethyl, 1-(2-methoxyethoxymethoxy) ethyl, 1-(ethoxymethoxy)ethyl, 1-acetoxyethyl, 1-propionyloxyethyl, 1-butyryloxyethyl, 1-valeryloxyethyl, 1-hexanoyloxyethyl, 1-heptanoyloxyethyl, 1-octanoyloxyethyl, 1-nonanoyloxyethyl, 1-(methoxyacetoxy)ethyl, 1-(phenoxyacetoxy)ethyl, 1-(phenylacetoxy)ethyl, 1-(3-phenylpropionyloxy)ethyl, 1-(2-thienylacetoxy)ethyl, 1-(2-furylacetoxy)ethyl, 1-methanesulfonyloxyethyl, 1-ethanesulfonyloxyethyl, 1-benzenesulfonyloxyethyl and methoxy groups.

Examples of preferred groups which may be represented by R$^2$ include the methyl, ethyl, isopropyl, methoxymethyl, phenyl and benzyl groups.

Examples of preferred groups which may be represented by R$^7$ include the hydrogen atom and the methyl, ethyl and ethoxymethyl groups.

Preferred classes of compounds of the present invention are exemplified as follows:

(A) Compounds of formula (Ia), wherein n is 0.

(B) Compounds of formula (I), wherein:

A and B are independently selected from the group consisting of ammine groups, C$_1$–C$_3$ alkylamine groups and arylamine groups in which the aryl part is a phenyl group which is unsubstituted or has at least one substituent selected from the group consisting of C$_1$–C$_4$ alkyl groups; or A and B together represent a compound of formula H$_2$N—Y—NH$_2$, where Y represents a C$_3$–C$_7$ alkylene group, a C$_6$ aromatic compound, a nitrogen-containing heterocyclic compound having from 5 to 8 ring atoms of which 1 is a nitrogen hetero-atom and 0 or 1 is an oxygen hetero-atom, a nitrogen-free heterocyclic compound having from 5 to 8 ring atoms of which 1 or 2 are hetero-atoms selected from the group consisting of oxygen and sulfur hetero-atoms or an alicyclic compound having from 5 to 8 ring atoms in a single ring or in a bridged ring, wherein said aromatic compound, said nitrogen-free heterocyclic compound and said alicyclic compound have two substituents selected from the group consisting of amino groups and C$_1$–C$_4$ aminoalkyl groups and wherein said nitrogen-containing heterocyclic compound has one substituent selected from the group consisting of amino groups and C$_1$–C$_4$ aminoalkyl groups;

and Z represents a group of formula (II):

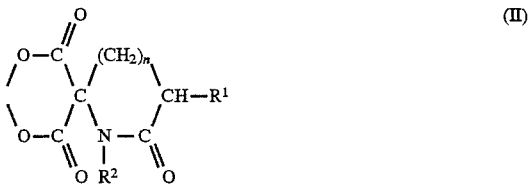

(II)

or a group of formula (III):

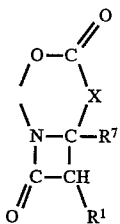

wherein:

R¹ represents a hydrogen atom, a $C_1$–$C_4$ alkyl group, a substituted $C_1$–$C_4$ alkyl group having at least one substituent selected from the group consisting of substituents (a), a $C_6$ carbocyclic aryl group, a $C_1$–$C_4$ alkyl group having at least one $C_6$ carbocyclic aryl substituent, a heterocyclic group having from 5 to 8 ring atoms of which in total from 1 to 4 are hetero-atoms selected from the group consisting of 0, 1, 2, 3 or 4 nitrogen atoms and 0, 1 or 2 oxygen or sulfur atoms, a $C_2$–$C_4$ aliphatic carboxylic acylamino group, a $C_7$ aromatic carboxylic acylamino group, a $C_2$–$C_4$ aliphatic carboxylic acylamino group having at least one $C_6$ carbocyclic aryl substituent, a $C_2$–$C_6$ alkoxycarbonyl group, a $C_1$–$C_4$ alkoxy group, a $C_1$–$C_4$ alkylthio group, a halogen atom, a cyano group or a phthalimido group, said heterocyclic groups and said $C_6$ carbocyclic aryl groups and substituents being unsubstituted or having at least one substituent selected from the group consisting of substituents (b);

R² represents a hydrogen atom, a $C_1$–$C_4$ alkyl group, a substituted $C_1$–$C_4$ alkyl group having at least one substituent selected from the group consisting of substituents (c), a $C_6$ carbocyclic aryl group, a $C_1$–$C_4$ alkyl group having at least one $C_6$ carbocyclic aryl substituent, said $C_6$ carbocyclic aryl groups and substituents being unsubstituted or having at least one substituent selected from the group consisting of substituents (c);

R⁷ represents a hydrogen atom, a $C_1$–$C_4$ alkyl group, a substituted $C_1$–$C_4$ alkyl group having at least one substituent selected from the group consisting of substituents (c), a $C_2$–$C_6$ alkoxycarbonyl group or a cyano group;

X represents a single carbon-carbon bond or a $C_1$–$C_3$ alkylene group;

n is 0, 1 or 2;

substituents (a) are selected from the group consisting of hydroxy groups, silyloxy groups having from 1 to 3 substituents on the silicon atom selected from the group consisting of $C_1$–$C_4$ alkyl groups and $C_6$ carbocyclic aryl groups which are unsubstituted or have at least one substituent selected from the group consisting of substituents (b), $C_1$–$C_4$ alkoxy groups, halogen atoms, groups of formula —OPO(OR³)₂, —OSO₂R³ and —O—COR⁴, and $C_2$–$C_5$ alkoxyalkoxy groups;

wherein:

R³ represents a $C_1$–$C_4$ alkyl group, a $C_6$ carbocyclic aryl group or a $C_6$ carbocyclic aryl group having at least one substituent selected from the group consisting of substituents (b) and (c), and R⁴ represents a $C_1$–$C_9$ alkyl group, a $C_2$–$C_5$ alkoxyalkyl group, a phenoxyalkyl group in which the alkyl part is $C_1$–$C_3$, an aralkyl group in which the alkyl part is $C_1$–$C_3$ and the aryl part is a $C_6$ carbocyclic aryl group which is unsubstituted or has at least one substituent selected from the group consisting of substituents (b) and (c), a $C_6$ carbocyclic aryl group which is unsubstituted or has at least one substituent selected from the group consisting of substituents (b) and (c), or a heterocyclic group having 5 or 6 ring atoms of which 1 or 2 are hetero-atoms selected from the group consisting of oxygen and nitrogen hetero-atoms, said heterocyclic groups being unsubstituted or having at least one substituent selected from the group consisting of substituents (b) and (c);

substituents (b) are selected from the group consisting of hydroxy groups, $C_1$–$C_4$ alkyl groups, $C_1$–$C_4$ alkoxy groups and halogen atoms; and substituents (c) are selected from the group consisting of $C_1$–$C_4$ alkyl groups, $C_1$–$C_4$ alkoxy groups, $C_1$–$C_4$ alkylthio groups, $C_2$–$C_5$ alkoxyalkoxy groups and halogen atoms;

PROVIDED THAT substituents (b) and (c) are not said alkyl groups when they are substituents on alkyl groups. (C) Compounds as in (B) above, wherein n is 0.

(D) Compounds of formula (In), wherein:

A and B are independently selected from the group consisting of ammine groups and $C_1$–$C_3$ alkylamine groups; or A and B together represent a compound of formula H₂N—Y—NH₂, where Y represents a $C_4$–$C_7$ alkylene group, a nitrogen-containing heterocyclic compound having from 5 to 6 ring atoms of which 1 is a nitrogen hetero-atom and 0 or 1 is an oxygen hetero-atom, a nitrogen-free heterocyclic compound having from 5 to 6 ring atoms of which 1 or 2 are oxygen hetero-atoms or an alicyclic compound having from 5 to 8 ring atoms in a single ring or in a bridged ring, wherein said nitrogen-free heterocyclic compound and said alicyclic compound have two substituents selected from the group consisting of amino groups and $C_1$–$C_2$ aminoalkyl groups and wherein said nitrogen-containing heterocyclic compound has one substituent selected from the group consisting of amino groups and $C_1$–$C_2$ aminoalkyl groups;

R¹ represents a hydrogen atom, a $C_1$–$C_4$ alkyl group, a phenyl group, a substituted $C_1$–$C_4$ alkyl group having at least one substituent selected from the group consisting of substituents (a'), a $C_1$–$C_4$ alkyl group having at least one phenyl substituent, a halogen atom or a cyano group, said phenyl group or substituent being unsubstituted or having at least one substituent selected from the group consisting of substituents (b);

R² represents a hydrogen atom, a $C_1$–$C_4$ alkyl group, a substituted $C_1$–$C_4$ alkyl group having at least one substituent selected from the group consisting of substituents (c') or a $C_1$–$C_4$ alkyl group having at least one phenyl substituent, said phenyl substituent being unsubstituted or having at least one substituent selected from the group consisting of substituents (b);

substituents (a') are selected from the group consisting of hydroxy groups, silyloxy groups having from 1 to 3 substituents on the silicon atom selected from the group consisting of $C_1$–$C_4$ alkyl groups and phenyl groups which are unsubstituted or have at least one substituent selected from the group consisting of substituents (b), $C_1$–$C_3$ alkoxy groups, halogen atoms and groups of formula —OPO(OR³)₂, —OSO₂R³ and —O—COR⁴;

wherein:

R³ represents a $C_1$–$C_4$ alkyl group, a phenyl group or a phenyl group having at least one substituent selected from the group consisting of substituents (b), and R⁴ represents a $C_1$–$C_9$ alkyl group, a $C_2$–$C_5$ alkoxyalkyl group, a phenoxyalkyl group in which the alkyl part is $C_1$–$C_3$, an aralkyl group in which the alkyl part is $C_1$–$C_3$ and the aryl part is a phenyl group which is unsubstituted or has at least one substituent selected from the group consisting of substituents (b), a phenyl group which is unsubstituted or has at least one substituent selected from the group consisting of substituents (b), or a heterocyclic group having 5 or 6 ring atoms of which 1 or 2 are hetero-atoms selected from the group consisting of oxygen and nitrogen hetero-atoms, said heterocyclic groups being unsubstituted or having at least one substituent selected from the group consisting of substituents (b); and substituents (c') are selected from the group consisting of $C_1$–$C_4$ alkyl groups, $C_1$–$C_4$ alkoxy groups, $C_2$–$C_5$ alkoxyalkoxy groups and halogen atoms;

PROVIDED THAT substituents (b) and (c') are not said alkyl groups when they are substituents on alkyl groups.

(E) Compounds as in (D) above, wherein n is 0.

(F) Compounds of formula (Ia), wherein:

A and B are independently selected from the group consisting of ammine groups and $C_1$–$C_3$ alkylamine groups; or A and B together represent a compound of formula $H_2N$—Y—$NH_2$, where Y represents a $C_5$–$C_7$ alkylene group, a nitrogen-containing heterocyclic compound having from 5 to 6 ring atoms of which 1 is a nitrogen hetero-atom or an alicyclic compound having from 5 to 8 ring atoms in a single ring or in a bridged ring, wherein said alicyclic compound has two substituents selected from the group consisting of amino groups and $C_1$–$C_2$ aminoalkyl groups and wherein said nitrogen-containing heterocyclic compound has one substituent selected from the group consisting of $C_1$–$C_2$ aminoalkyl groups;

$R^1$ represents: a hydrogen atom; a $C_1$–$C_4$ alkyl group; a substituted $C_1$–$C_4$ alkyl group having at least one substituent selected from the group consisting of $C_1$–$C_3$ alkoxy groups, $C_2$–$C_5$ alkoxyalkoxy groups and silyloxy groups having 3 substituents on the silicon atom selected from the group consisting of $C_1$–$C_4$ alkyl groups and phenyl groups; a phenyl group; a halogen atom; or a cyano group;

$R^2$ represents a hydrogen atom, a $C_1$–$C_2$ alkyl group or a substituted $C_1$–$C_2$ alkyl group having at least one substituent selected from the group consisting of $C_1$–$C_2$ alkoxy groups and $C_2$–$C_5$ alkoxyalkoxy groups; and n is 0.

(G) Compounds of formula (Ia), wherein:

A and B are independently selected from the group consisting of ammine groups and $C_3$ alkylamine groups; or A and B together represent a compound of formula $H_2N$—Y—$NH_2$, where Y represents a $C_3$–$C_4$ straight chain alkylene group having one or two substituents selected from the group consisting of methyl and ethyl groups, a nitrogen-containing heterocyclic compound having from 5 to 6 ring atoms of which 1 is a nitrogen hetero-atom or an alicyclic compound having from 5 to 8 ring atoms in a single ring, wherein said alicyclic compound has two substituents selected from the group consisting of amino groups and aminomethyl groups and wherein said nitrogen-containing heterocyclic compound has one substituent selected from the group consisting of aminomethyl groups;

$R^1$ represents a hydrogen atom, a $C_1$–$C_4$ alkyl group, a substituted $C_1$–$C_4$ alkyl group having at least one substituent selected from the group consisting of $C_1$–$C_2$ alkoxy groups, $C_2$–$C_5$ alkoxyalkoxy groups and silyloxy groups having 3 substituents on the silicon atom selected from the group consisting of $C_1$–$C_4$ alkyl groups, a phenyl group or a halogen atom;

$R^2$ represents a hydrogen atom, a $C_1$–$C_2$ alkyl group or a substituted $C_1$–$C_2$ alkyl group having at least one substituent selected from the group consisting of $C_1$–$C_2$ alkoxy groups and $C_2$–$C_5$ alkoxyalkoxy groups; and n is 0.

(H) Compounds of formula (Ib), wherein:

A and B are independently selected from the group consisting of ammine groups and $C_1$–$C_3$ alkylamine groups; or A and B together represent a compound of formula $H_2N$—Y—$NH_2$, where Y represents a $C_4$–$C_7$ alkylene group, a nitrogen-containing heterocyclic compound having from 5 to 6 ring atoms of which 1 is a nitrogen hetero-atom and 0 or 1 is an oxygen hetero-atom, a nitrogen-free heterocyclic compound having from 5 to 6 ring atoms of which 1 or 2 are oxygen hetero-atoms or an alicyclic compound having from 5 to 8 ring atoms in a single ring or in a bridged ring, wherein said nitrogen-free heterocyclic compound and said alicyclic compound have two substituents selected from the group consisting of amino groups and $C_1$–$C_2$ aminoalkyl groups and wherein said nitrogen-containing heterocyclic compound has one substituent selected from the group consisting of amino groups and $C_1$–$C_2$ aminoalkyl groups;

$R^1$ represents a hydrogen atom, a $C_1$–$C_4$ alkyl group, a $C_1$–$C_4$ alkoxy group, a phenyl group, a substituted $C_1$–$C_4$ alkyl group having at least one substituent selected from the group consisting of substituents (a"), a $C_1$–$C_4$ alkyl group having at least one phenyl substituent, a halogen atom or a cyano group, said phenyl group or substituent being unsubstituted or having at least one substituent selected from the group consisting of substituents (b);

$R^7$ represents a hydrogen atom, a $C_1$–$C_4$ alkyl group or a $C_2$–$C_6$ alkoxycarbonyl group;

substituents (a") are selected from the group consisting of hydroxy groups, silyloxy groups having from 1 to 3 substituents on the silicon atom selected from the group consisting of $C_1$–$C_4$ alkyl groups and phenyl groups which are unsubstituted or have at least one substituent selected from the group consisting of substituents (b), $C_1$–$C_3$ alkoxy groups, $C_2$–$C_5$ alkoxyalkoxy groups, $C_3$–$C_7$ alkoxyalkoxyalkoxy groups, halogen atoms and groups of formula —OPO(OR$^3$)$_2$, —OSO$_2$R$^3$ and wherein:

$R^3$ represents a $C_1$–$C_4$ alkyl group, a phenyl group or a phenyl group having at least one substituent selected from the group consisting of $C_1$–$C_4$ alkyl groups, and $R^4$ represents a $C_1$–$C_8$ alkyl group, a $C_2$–$C_5$ alkoxyalkyl group, a phenoxyalkyl group in which the alkyl part is $C_1$–$C_3$, an aralkyl group in which the alkyl part is $C_1$–$C_3$ and the aryl part is a phenyl group which is unsubstituted or has at least one substituent selected from the group consisting of substituents (b), a phenyl group which is unsubstituted or has at least one substituent selected from the group consisting of substituents (b), or a heterocyclic group having 5 or 6 ring atoms of which 1 or 2 are hetero-atoms selected from the group consisting of oxygen and nitrogen hetero-atoms, said heterocyclic groups being unsubstituted or having at least one substituent selected from the group consisting of substituents (b).

(I) Compounds as in (H) above, wherein X is a direct bond or a methylene group.

(J) Compounds of formula (Ib), wherein:

A and B are independently selected from the group consisting of ammine groups and $C_1$–$C_3$ alkylamine groups; or A and B together represent a compound of formula $H_2N$—Y—$NH_2$, where Y represents a $C_5$–$C_7$ alkylene group, a nitrogen-containing heterocyclic compound having from to 6 ring atoms of which 1 is a nitrogen hetero-atom or an alicyclic compound having from 5 to 8 ring atoms in a single ring or in a bridged ring, wherein said alicyclic compound has two substituents selected from the group consisting of amino groups and $C_1$–$C_2$ aminoalkyl groups and wherein said nitrogen-containing heterocyclic compound has one substituent selected from the group consisting of $C_1$–$C_2$ aminoalkyl groups;

$R^1$ represents a hydrogen atom, a $C_1$–$C_4$ alkyl group, a $C_1$–$C_4$ alkoxy group, a substituted $C_1$–$C_4$ alkyl group having at least one substituent selected from the group consisting of substituents (a'''), a halogen atom or a cyano group:

$R^7$ represents a hydrogen atom or a $C_2$–$C_5$ alkoxycarbonyl group;

substituents (a''') are selected from the group consisting of silyloxy groups having 3 substituents on the silicon atom selected from the group consisting of $C_1$–$C_4$ alkyl groups and phenyl groups, $C_1$–$C_3$ alkoxy groups, $C_2$–$C_5$ alkoxyalkoxy groups, $C_3$–$C_7$ alkoxyalkoxyalkoxy groups and groups of formula —OPO(OR$^3$)$_2$, —OSO$_2$R$^3$ and —O—COR$^4$;
wherein:

$R^3$ represents a $C_1$–$C_3$ alkyl group or a phenyl group, and $R^4$ represents a $C_1$–$C_8$ alkyl group, a $C_2$–$C_5$ alkoxyalkyl group, a phenoxyalkyl group in which the alkyl part is $C_1$–$C_3$, an aralkyl group in which the alkyl part is $C_1$–$C_3$ and the aryl part is a phenyl group or a phenyl group which is unsubstituted or has at least one substituent selected from the group consisting of $C_1$–$C_4$ alkyl groups.

(K) Compounds as in (J) above, wherein X is a direct bond or a methylene group.

(L) Compounds of formula (Ib), wherein:

A and B are independently selected from the group consisting of ammine groups and $C_3$ alkylamine groups; or A and B together represent a compound of formula $H_2N$—Y—$NH_2$, where Y represents a $C_3$–$C_4$ straight chain alkylene group having one or two substituents selected from the group consisting of methyl and ethyl groups, a nitrogen-containing heterocyclic compound having from 5 to 6 ring atoms of which 1 is a nitrogen hetero-atom or an alicyclic compound having from 5 to 8 ring atoms in a single ring, wherein said alicyclic compound has two substituents selected from the group consisting of amino groups and $C_1$–$C_2$ aminoalkyl groups and wherein said nitrogen-containing heterocyclic compound has one substituent selected from the group consisting of $C_1$–$C_2$ aminoalkyl groups:

$R^1$ represents a hydrogen atom, a $C_1$–$C_2$ alkyl group, a $C_1$–$C_2$ alkoxy group, a substituted $C_1$–$C_4$ alkyl group having at least one substituent selected from the group consisting of substituents (a$^{iv}$) or a halogen atom;

$R^7$ represents a hydrogen atom or a $C_2$–$C_5$ alkoxycarbonyl group;

substituents (a$^{iv}$) are selected from the group consisting of silyloxy groups having 3 substituents on the silicon atom selected from the group consisting of $C_1$–$C_4$ alkyl groups, $C_1$–$C_3$ alkoxy groups, $C_2$–$C_5$ alkoxyalkoxy groups, $C_3$–$C_7$ alkoxyalkoxyalkoxy groups and groups of formula —OPO(OR$^3$)$_2$, —OSO$_2$R$^3$ and —O—COR$^4$;
wherein:

$R^3$ represents a $C_1$–$C_3$ alkyl group or a phenyl group, and $R^4$ represents a $C_1$–$C_8$ alkyl group, a $C_2$–$C_3$ alkoxyalkyl group, a phenoxymethyl group or a benzyl group.

(M) Compounds as in (h) above, wherein X is a direct bond or a methylene group.

(N) Compounds of formulae (I), (Ia) and (Ib), wherein $R^3$ represents a $C_1$–$C_4$ alkyl group, a $C_6$–$C_{10}$ aryl group or a $C_6$–$C_{10}$ aryl group having at least one substituent selected from the group consisting of $C_1$–$C_4$ alkyl groups.

(O) Compounds of formulae (I), (Ia) and (Ib), wherein $R^4$ represents an unsubstituted heterocyclic group.

(P) Compounds of formulae (I), (Ia) and (Ib), wherein $R^4$ represents a thienyl or furyl group.

In general above, where reference is made to "substituted" groups, there is no restriction upon the number of substituents, except, as would be well recognised by those skilled in the art, those imposed by the number of substitutable positions and/or by steric constraints. In most cases, however, we generally would not expect to exceed 3 such substituents (although only for reasons of convenience and not associated with the essence of the invention), and normally, in the present case, one such substituent is preferred, except where otherwise noted.

The compounds of the present invention can exist in the form of various geometric isomers about the platinum atom and possibly because of asymmetric carbon atoms in groups within the compounds. The present invention embraces both the individual isolated isomers, as well as mixtures thereof. Individual isomers may be prepared by stereo-specific synthesis techniques, or they may be prepared by separation of mixtures of isomers, as is well recognised in the art. It is also well known that some isomers may be more active than others, and this may be determined with ease in respect of any particular pair of isomers, using standard laboratory techniques.

Examples of specific compounds of the invention are given in the following formulae (I-1) to (I-5), in which the substituents are as defined in the corresponding one of Tables 1 to 5 [i.e. Table 1 relates to formula (I-1), Table 2 relates to formula (I-2) and so on]. In the Tables, the following abbreviations are used:

| | |
|---|---|
| Ac | acetyl |
| Bes | benzenesulfonyl |
| tBu | t-butyl |
| Byr | butyryl |
| Bz | benzyl |
| Et | ethyl or ethylene, as the context requires |
| Hpo | heptanoyl |
| cHx | cyclohexyl |
| Hxo | hexanoyl |
| Me | methyl or methylene, as the context requires |
| Mes | methanesulfonyl |
| cOc | cyclooctyl |
| Octo | octanoyl |
| Ph | phenyl |
| Pr | propyl |
| iPr | isopropyl |
| Prn | propionyl |
| Pyrd | pyrrolidinyl |
| Va | valeryl |

In Tables 4 and 5, in the column for X, a dash (—) indicates a direct bond.

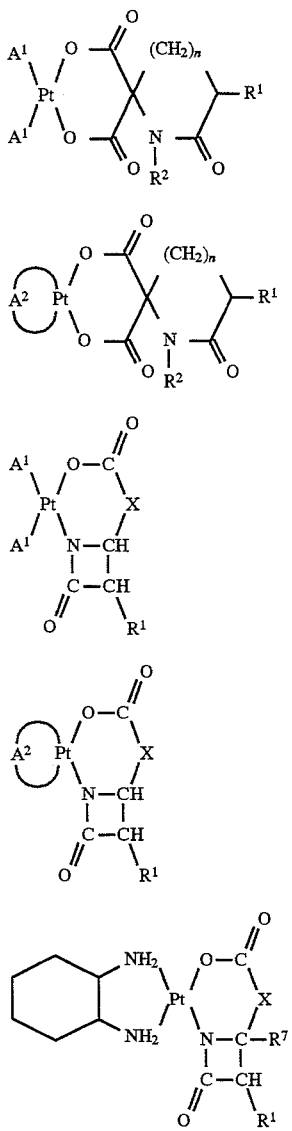

(I-1)

(I-2)

(I-3)

(I-4)

(I-5)

TABLE 1

| Cpd. No. | n | $A^1$ | $R^1$ | $R^2$ |
|---|---|---|---|---|
| 1-1 | 0 | $H_3N$ | H | H |
| 1-2 | 0 | $H_3N$ | Me | H |
| 1-3 | 0 | $H_3N$ | H | Me |
| 1-4 | 0 | $H_3N$ | Me | Me |
| 1-5 | 0 | $H_3N$ | H | MeOMe |
| 1-6 | 0 | $H_3N$ | H | 2-MeOEtOMe |
| 1-7 | 0 | $H_3N$ | Br | H |
| 1-8 | 0 | $H_3N$ | Ph | H |
| 1-9 | 0 | $H_3N$ | iPr | H |
| 1-10 | 0 | $H_3N$ | iPr | Me |
| 1-11 | 0 | $H_3N$ | iPr | MeOMe |
| 1-12 | 0 | $H_3N$ | MeOMe | H |
| 1-13 | 0 | $H_3N$ | Bz | H |
| 1-14 | 0 | $H_3N$ | 1-MeOEt | H |
| 1-15 | 0 | $H_3N$ | 1-MeOEt | Me |
| 1-16 | 0 | $H_3N$ | 1-MeOEt | MeOMe |
| 1-17 | 1 | $H_3N$ | H | H |
| 1-18 | 2 | $H_3N$ | H | H |
| 1-19 | 0 | $iPrNH_2$ | H | H |
| 1-20 | 0 | $iPrNH_2$ | Me | H |
| 1-21 | 0 | $iPrNH_2$ | H | Me |
| 1-22 | 0 | $iPrNH_2$ | Me | Me |

TABLE 1-continued

| Cpd. No. | n | $A^1$ | $R^1$ | $R^2$ |
|---|---|---|---|---|
| 1-23 | 0 | $iPrNH_2$ | H | MeOMe |
| 1-24 | 0 | $iPrNH_2$ | H | 2-MeOEtOMe |
| 1-25 | 0 | $iPrNH_2$ | Br | H |
| 1-26 | 0 | $iPrNH_2$ | Ph | H |
| 1-27 | 0 | $iPrNH_2$ | iPr | H |
| 1-28 | 0 | $iPrNH_2$ | iPr | Me |
| 1-29 | 0 | $iPrNH_2$ | iPr | MeOMe |
| 1-30 | 0 | $iPrNH_2$ | MeOMe | H |
| 1-31 | 0 | $iPrNH_2$ | Bz | H |
| 1-32 | 0 | $iPrNH_2$ | 1-MeOEt | H |
| 1-33 | 0 | $iPrNH_2$ | 1-MeOEt | Me |
| 1-34 | 0 | $iPrNH_2$ | 1-MeOEt | MeOMe |
| 1-35 | 1 | $iPrNH_2$ | H | H |
| 1-36 | 2 | $iPrNH_2$ | H | H |

TABLE 2

| Cpd No. | n | $R^1$ | $R^2$ | $A^2$ |
|---|---|---|---|---|
| 2-1 | 0 | H | H | $H_2N(CH_2)_2CH(Me)CH_2NH_2$ |
| 2-2 | 0 | Me | H | $H_2N(CH_2)_2CH(Me)CH_2NH_2$ |
| 2-3 | 0 | H | Me | $H_2N(CH_2)_2CH(Me)CH_2NH_2$ |
| 2-4 | 0 | Me | Me | $H_2N(CH_2)_2CH(Me)CH_2NH_2$ |
| 2-5 | 0 | H | MeOMe | $H_2N(CH_2)_2CH(Me)CH_2NH_2$ |
| 2-6 | 0 | H | 2-MeOEtOMe | $H_2N(CH_2)_2CH(Me)CH_2NH_2$ |
| 2-7 | 0 | Br | H | $H_2N(CH_2)_2CH(Me)CH_2NH_2$ |
| 2-8 | 0 | Ph | H | $H_2N(CH_2)_2CH(Me)CH_2NH_2$ |
| 2-9 | 0 | iPr | H | $H_2N(CH_2)_2CH(Me)CH_2NH_2$ |
| 2-10 | 0 | iPr | Me | $H_2N(CH_2)_2CH(Me)CH_2NH_2$ |
| 2-11 | 0 | iPr | MeOMe | $H_2N(CH_2)_2CH(Me)CH_2NH_2$ |
| 2-12 | 0 | MeOMe | H | $H_2N(CH_2)_2CH(Me)CH_2NH_2$ |
| 2-13 | 0 | Bz | H | $H_2N(CH_2)_2CH(Me)CH_2NH_2$ |
| 2-14 | 0 | 1-MeOEt | H | $H_2N(CH_2)_2CH(Me)CH_2NH_2$ |
| 2-15 | 0 | 1-MeOEt | Me | $H_2N(CH_2)_2CH(Me)CH_2NH_2$ |
| 2-16 | 0 | 1-MeOEt | MeOMe | $H_2N(CH_2)_2CH(Me)CH_2NH_2$ |
| 2-17 | 1 | H | H | $H_2N(CH_2)_2CH(Me)CH_2NH_2$ |
| 2-18 | 2 | H | H | $H_2N(CH_2)_2CH(Me)CH_2NH_2$ |
| 2-19 | 0 | H | H | 1,2-diNH$_2$cHx |
| 2-20 | 0 | Me | H | 1,2-diNH$_2$cHx |
| 2-21 | 0 | H | Me | 1,2-diNH$_2$cHx |
| 2-22 | 0 | Me | Me | 1,2-diNH$_2$cHx |
| 2-23 | 0 | H | MeOMe | 1,2-diNH$_2$cHx |
| 2-24 | 0 | H | 2-MeOEtOMe | 1,2-diNH$_2$cHx |
| 2-25 | 0 | Br | H | 1,2-diNH$_2$cHx |
| 2-26 | 0 | Ph | H | 1,2-diNH$_2$cHx |
| 2-27 | 0 | iPr | H | 1,2-diNH$_2$cHx |
| 2-28 | 0 | iPr | Me | 1,2-diNH$_2$cHx |
| 2-29 | 0 | iPr | MeOMe | 1,2-diNH$_2$cHx |
| 2-30 | 0 | MeOMe | H | 1,2-diNH$_2$cHx |
| 2-31 | 0 | Bz | H | 1,2-diNH$_2$cHx |
| 2-32 | 0 | 1-MeOEt | H | 1,2-diNH$_2$cHx |
| 2-33 | 0 | 1-MeOEt | Me | 1,2-diNH$_2$cHx |
| 2-34 | 0 | 1-MeOEt | MeOMe | 1,2-diNH$_2$cHx |
| 2-35 | 1 | H | H | 1,2-diNH$_2$cHx |
| 2-36 | 2 | H | H | 1,2-diNH$_2$cHx |
| 2-37 | 0 | H | H | 1-NH$_2$-2-NH$_2$MecHx |
| 2-38 | 0 | Me | H | 1-NH$_2$-2-NH$_2$MecHx |
| 2-39 | 0 | H | Me | 1-NH$_2$-2-NH$_2$MecHx |
| 2-40 | 0 | Me | Me | 1-NH$_2$-2-NH$_2$MecHx |
| 2-41 | 0 | H | MeOMe | 1-NH$_2$-2-NH$_2$MecHx |
| 2-42 | 0 | H | 2-MeOEtOMe | 1-NH$_2$-2-NH$_2$MecHx |
| 2-43 | 0 | Br | H | 1-NH$_2$-2-NH$_2$MecHx |
| 2-44 | 0 | Ph | H | 1-NH$_2$-2-NH$_2$MecHx |
| 2-45 | 0 | iPr | H | 1-NH$_2$-2-NH$_2$MecHx |
| 2-46 | 0 | iPr | Me | 1-NH$_2$-2-NH$_2$MecHx |
| 2-47 | 0 | iPr | MeOMe | 1-NH$_2$-2-NH$_2$MecHx |
| 2-48 | 0 | MeOMe | H | 1-NH$_2$-2-NH$_2$MecHx |
| 2-49 | 0 | Bz | H | 1-NH$_2$-2-NH$_2$MecHx |
| 2-50 | 0 | 1-MeOEt | H | 1-NH$_2$-2-NH$_2$MecHx |

TABLE 2-continued

| Cpd No. | n | R¹ | R² | A² |
|---|---|---|---|---|
| 2-51 | 0 | 1-MeOEt | Me | 1-NH₂-2-NH₂MecHx |
| 2-52 | 0 | 1-MeOEt | MeOMe | 1-NH₂-2-NH₂MecHx |
| 2-53 | 1 | H | H | 1-NH₂-2-NH₂MecHx |
| 2-54 | 2 | H | H | 1-NH₂-2-NH₂MecHx |
| 2-55 | 0 | H | H | 2-NH₂MePyrd |
| 2-56 | 0 | Me | H | 2-NH₂MePyrd |
| 2-57 | 0 | H | Me | 2-NH₂MePyrd |
| 2-58 | 0 | Me | Me | 2-NH₂MePyrd |
| 2-59 | 0 | H | MeOMe | 2-NH₂MePyrd |
| 2-60 | 0 | H | 2-MeOEtOMe | 2-NH₂MePyrd |
| 2-61 | 0 | Br | H | 2-NH₂MePyrd |
| 2-62 | 0 | Ph | H | 2-NH₂MePyrd |
| 2-63 | 0 | iPr | H | 2-NH₂MePyrd |
| 2-64 | 0 | iPr | Me | 2-NH₂MePyrd |
| 2-65 | 0 | iPr | MeOMe | 2-NH₂MePyrd |
| 2-66 | 0 | MeOMe | H | 2-NH₂MePyrd |
| 2-67 | 0 | Bz | H | 2-NH₂MePyrd |
| 2-68 | 0 | 1-MeOEt | H | 2-NH₂MePyrd |
| 2-69 | 0 | 1-MeOEt | Me | 2-NH₂MePyrd |
| 2-70 | 0 | 1-MeOEt | MeOMe | 2-NH₂MePyrd |
| 2-71 | 1 | H | H | 2-NH₂MePyrd |
| 2-72 | 2 | H | H | 2-NH₂MePyrd |
| 2-73 | 0 | H | H | 1,3-diNH₂-2,2-diEtPr |
| 2-74 | 0 | Me | H | 1,3-diNH₂-2,2-diEtPr |
| 2-75 | 0 | H | Me | 1,3-diNH₂-2,2-diEtPr |
| 2-76 | 0 | Me | Me | 1,3-diNH₂-2,2-diEtPr |
| 2-77 | 0 | H | MeOMe | 1,3-diNH₂-2,2-diEtPr |
| 2-78 | 0 | H | 2-MeOEtOMe | 1,3-diNH₂-2,2-diEtPr |
| 2-79 | 0 | Br | H | 1,3-diNH₂-2,2-diEtPr |
| 2-80 | 0 | Ph | H | 1,3-diNH₂-2,2-diEtPr |
| 2-81 | 0 | iPr | H | 1,3-diNH₂-2,2-diEtPr |
| 2-82 | 0 | iPr | Me | 1,3-diNH₂-2,2-diEtPr |
| 2-83 | 0 | iPr | MeOMe | 1,3-diNH₂-2,2-diEtPr |
| 2-84 | 0 | MeOMe | H | 1,3-diNH₂-2,2-diEtPr |
| 2-85 | 0 | Bz | H | 1,3-diNH₂-2,2-diEtPr |
| 2-86 | 0 | 1-MeOEt | H | 1,3-diNH₂-2,2-diEtPr |
| 2-87 | 0 | 1-MeOEt | Me | 1,3-diNH₂-2,2-diEtPr |
| 2-88 | 0 | 1-MeOEt | MeOMe | 1,3-diNH₂-2,2-diEtPr |
| 2-89 | 1 | H | H | 1,3-diNH₂-2,2-diEtPr |
| 2-90 | 2 | H | H | 1,3-diNH₂-2,2-diEtPr |
| 2-91 | 0 | H | H | 1,2-diNH₂cOc |
| 2-92 | 0 | Me | H | 1,2-diNH₂cOc |
| 2-93 | 0 | H | Me | 1,2-diNH₂cOc |
| 2-94 | 0 | Me | Me | 1,2-diNH₂cOc |
| 2-95 | 0 | H | MeOMe | 1,2-diNH₂cOc |
| 2-96 | 0 | H | 2-MeOEtOMe | 1,2-diNH₂cOc |
| 2-97 | 0 | Br | H | 1,2-diNH₂cOc |
| 2-98 | 0 | Ph | H | 1,2-diNH₂cOc |
| 2-99 | 0 | iPr | H | 1,2-diNH₂cOc |
| 2-100 | 0 | iPr | Me | 1,2-diNH₂cOc |
| 2-101 | 0 | iPr | MeOMe | 1,2-diNH₂cOc |
| 2-102 | 0 | MeOMe | H | 1,2-diNH₂cOc |
| 2-103 | 0 | Bz | H | 1,2-diNH₂cOc |
| 2-104 | 0 | 1-MeOEt | H | 1,2-diNH₂cOc |
| 2-105 | 0 | 1-MeOEt | Me | 1,2-diNH₂cOc |
| 2-106 | 0 | 1-MeOEt | MeOMe | 1,2-diNH₂cOc |
| 2-107 | 1 | H | H | 1,2-diNH₂cOc |
| 2-108 | 2 | H | H | 1,2-diNH₂cOc |

TABLE 3

| Cpd No. | X | A¹ | R¹ |
|---|---|---|---|
| 3-1 | — | H₃N | 1-HOEt |
| 3-2 | — | H₃N | 1-(OSiMe₃)Et |
| 3-3 | — | H₃N | 1-(OSiMe₂tBu)Et |
| 3-4 | — | H₃N | 1-[OPO(OEt)₂]Et |
| 3-5 | — | H₃N | 1-[OPO(OPh)₂]Et |
| 3-6 | — | H₃N | 1-AcOEt |
| 3-7 | — | H₃N | 1-PmOEt |
| 3-8 | — | H₃N | 1-ByrOEt |
| 3-9 | — | H₃N | 1-VaOEt |
| 3-10 | — | H₃N | 1-HxoOEt |
| 3-11 | — | H₃N | 1-HpoOEt |
| 3-12 | — | H₃N | 1-(OctoO)Et |
| 3-13 | — | H₃N | 1-BzOEt |
| 3-14 | — | H₃N | 1-(MeOAcO)Et |
| 3-15 | — | H₃N | 1-(PhOAcO)Et |
| 3-16 | — | H₃N | 1-(PhAcO)Et |
| 3-17 | — | H₃N | 1-MeOEt |
| 3-18 | — | H₃N | 1-(MeOMeO)Et |
| 3-19 | — | H₃N | 1-[MeOEtOMeO]Et |
| 3-20 | — | H₃N | 1-MesOEt |
| 3-21 | — | H₃N | 1-BesOEt |
| 3-22 | CH₂ | iPrNH₂ | 1-HOEt |
| 3-23 | CH₂ | iPrNH₂ | 1-(OSiMe₃)Et |
| 3-24 | CH₂ | iPrNH₂ | 1-(OSiMe₂tBu)Et |
| 3-25 | CH₂ | iPrNH₂ | 1-[OPO(OEt)₂]Et |
| 3-26 | CH₂ | iPrNH₂ | 1-[OPO(OPh)₂]Et |
| 3-27 | CH₂ | iPrNH₂ | 1-AcOEt |
| 3-28 | CH₂ | iPrNH₂ | 1-PmOEt |
| 3-29 | CH₂ | iPrNH₂ | 1-ByrOEt |
| 3-30 | CH₂ | iPrNH₂ | 1-VaOEt |
| 3-31 | CH₂ | iPrNH₂ | 1-HxoOEt |
| 3-32 | CH₂ | iPrNH₂ | 1-HpoOEt |
| 3-33 | CH₂ | iPrNH₂ | 1-(OctoO)Et |
| 3-34 | CH₂ | iPrNH₂ | 1-BzOEt |
| 3-35 | CH₂ | iPrNH₂ | 1-(MeOAcO)Et |
| 3-36 | CH₂ | iPrNH₂ | 1-(PhOAcO)Et |
| 3-37 | CH₂ | iPrNH₂ | 1-(PhAcO)Et |
| 3-38 | CH₂ | iPrNH₂ | 1-MeOEt |
| 3-39 | CH₂ | iPrNH₂ | 1-(MeOMeO)Et |
| 3-40 | CH₂ | iPrNH₂ | 1-[MeOEtOMeO]Et |
| 3-41 | CH₂ | iPrNH₂ | 1-MesOEt |
| 3-42 | CH₂ | iPrNH₂ | 1-BesOEt |
| 3-43 | CH₂ | H₃N | 1-HOEt |
| 3-44 | CH₂ | H₃N | 1-(OSiMe₃)Et |
| 3-45 | CH₂ | H₃N | 1-(OSiMe₂tBu)Et |
| 3-46 | CH₂ | H₃N | 1-[OPO(OEt)₂]Et |
| 3-47 | CH₂ | H₃N | 1-[OPO(OPh)₂]Et |
| 3-48 | CH₂ | H₃N | 1-AcOEt |
| 3-49 | CH₂ | H₃N | 1-PmOEt |
| 3-50 | CH₂ | H₃N | 1-ByrOEt |
| 3-51 | CH₂ | H₃N | 1-VaOEt |
| 3-52 | CH₂ | H₃N | 1-HxoOEt |
| 3-53 | CH₂ | H₃N | 1-HpoOEt |
| 3-54 | CH₂ | H₃N | 1-(OctoO)Et |
| 3-55 | CH₂ | H₃N | 1-BzOEt |
| 3-56 | CH₂ | H₃N | 1-(MeOAcO)Et |
| 3-57 | CH₂ | H₃N | 1-(PhOAcO)Et |
| 3-58 | CH₂ | H₃N | 1-(PhAcO)Et |
| 3-59 | CH₂ | H₃N | 1-MeOEt |
| 3-60 | CH₂ | H₃N | 1-(MeOMeO)Et |
| 3-61 | CH₂ | H₃N | 1-[MeOEtOMeO]Et |
| 3-62 | CH₂ | H₃N | 1-MesOEt |
| 3-63 | CH₂ | H₃N | 1-BesOEt |

TABLE 4

| Cpd No. | X | R¹ | A² |
|---|---|---|---|
| 4-1 | — | 1-HOEt | H₂N(CH₂)₂CH(Me)CH₂NH₂ |
| 4-2 | — | 1-(OSiMe₃)Et | H₂N(CH₂)₂CH(Me)CH₂NH₂ |
| 4-3 | — | 1-(OSiMe₂tBu)Et | H₂N(CH₂)₂CH(Me)CH₂NH₂ |
| 4-4 | — | 1-[OPO(OEt)₂]Et | H₂N(CH₂)₂CH(Me)CH₂NH₂ |
| 4-5 | — | 1-[OPO(OPh)₂]Et | H₂N(CH₂)₂CH(Me)CH₂NH₂ |
| 4-6 | — | 1-AcOEt | H₂N(CH₂)₂CH(Me)CH₂NH₂ |
| 4-7 | — | 1-PmOEt | H₂N(CH₂)₂CH(Me)CH₂NH₂ |
| 4-8 | — | 1-ByrOEt | H₂N(CH₂)₂CH(Me)CH₂NH₂ |
| 4-9 | — | 1-VaOEt | H₂N(CH₂)₂CH(Me)CH₂NH₂ |
| 4-10 | — | 1-HxoOEt | H₂N(CH₂)₂CH(Me)CH₂NH₂ |

TABLE 4-continued

| Cpd No. | X | R¹ | A² |
|---|---|---|---|
| 4-11 | — | 1-HpoOEt | $H_2N(CH_2)_2CH(Me)CH_2NH_2$ |
| 4-12 | — | 1-(OctoO)Et | $H_2N(CH_2)_2CH(Me)CH_2NH_2$ |
| 4-13 | — | 1-BzOEt | $H_2N(CH_2)_2CH(Me)CH_2NH_2$ |
| 4-14 | — | 1-(MeOAcO)Et | $H_2N(CH_2)_2CH(Me)CH_2NH_2$ |
| 4-15 | — | 1-(PhOAcO)Et | $H_2N(CH_2)_2CH(Me)CH_2NH_2$ |
| 4-16 | — | 1-(PhAcO)Et | $H_2N(CH_2)_2CH(Me)CH_2NH_2$ |
| 4-17 | — | 1-MeOEt | $H_2N(CH_2)_2CH(Me)CH_2NH_2$ |
| 4-18 | — | 1-(MeOMeO)Et | $H_2N(CH_2)_2CH(Me)CH_2NH_2$ |
| 4-19 | — | 1-[MeOEtOMeO]Et | $H_2N(CH_2)_2CH(Me)CH_2NH_2$ |
| 4-20 | — | 1-MesOEt | $H_2N(CH_2)_2CH(Me)CH_2NH_2$ |
| 4-21 | — | 1-BesOEt | $H_2N(CH_2)_2CH(Me)CH_2NH_2$ |
| 4-22 | $CH_2$ | 1-HOEt | $H_2N(CH_2)_2CH(Me)CH_2NH_2$ |
| 4-23 | $CH_2$ | 1-(OSiMe₃)Et | $H_2N(CH_2)_2CH(Me)CH_2NH_2$ |
| 4-24 | $CH_2$ | 1-(OSiMe₂tBu)Et | $H_2N(CH_2)_2CH(Me)CH_2NH_2$ |
| 4-25 | $CH_2$ | 1-[OPO(OEt)₂]Et | $H_2N(CH_2)_2CH(Me)CH_2NH_2$ |
| 4-26 | $CH_2$ | 1-[OPO(OPh)₂]Et | $H_2N(CH_2)_2CH(Me)CH_2NH_2$ |
| 4-27 | $CH_2$ | 1-AcOEt | $H_2N(CH_2)_2CH(Me)CH_2NH_2$ |
| 4-28 | $CH_2$ | 1-PrnOEt | $H_2N(CH_2)_2CH(Me)CH_2NH_2$ |
| 4-29 | $CH_2$ | 1-ByrOEt | $H_2N(CH_2)_2CH(Me)CH_2NH_2$ |
| 4-30 | $CH_2$ | 1-VaOEt | $H_2N(CH_2)_2CH(Me)CH_2NH_2$ |
| 4-31 | $CH_2$ | 1-HxoOEt | $H_2N(CH_2)_2CH(Me)CH_2NH_2$ |
| 4-32 | $CH_2$ | 1-HpoOEt | $H_2N(CH_2)_2CH(Me)CH_2NH_2$ |
| 4-33 | $CH_2$ | 1-(OctoO)Et | $H_2N(CH_2)_2CH(Me)CH_2NH_2$ |
| 4-34 | $CH_2$ | 1-BzOEt | $H_2N(CH_2)_2CH(Me)CH_2NH_2$ |
| 4-35 | $CH_2$ | 1-(MeOAcO)Et | $H_2N(CH_2)_2CH(Me)CH_2NH_2$ |
| 4-36 | $CH_2$ | 1-(PhOAcO)Et | $H_2N(CH_2)_2CH(Me)CH_2NH_2$ |
| 4-37 | $CH_2$ | 1-(PhAcO)Et | $H_2N(CH_2)_2CH(Me)CH_2NH_2$ |
| 4-38 | $CH_2$ | 1-MeOEt | $H_2N(CH_2)_2CH(Me)CH_2NH_2$ |
| 4-39 | $CH_2$ | 1-(MeOMeO)Et | $H_2N(CH_2)_2CH(Me)CH_2NH_2$ |
| 4-40 | $CH_2$ | 1-[MeOEtOMeO]Et | $H_2N(CH_2)_2CH(Me)CH_2NH_2$ |
| 4-41 | $CH_2$ | 1-MesOEt | $H_2N(CH_2)_2CH(Me)CH_2NH_2$ |
| 4-42 | $CH_2$ | 1-BesOEt | $H_2N(CH_2)_2CH(Me)CH_2NH_2$ |
| 4-43 | — | 1-HOEt | 1,2-diNH₂cHx |
| 4-44 | — | 1-(OSiMe₃)Et | 1,2-diNH₂cHx |
| 4-45 | — | 1-(OSiMe₂tBu)Et | 1,2-diNH₂cHx |
| 4-46 | — | 1-[OPO(OEt)₂]Et | 1,2-diNH₂cHx |
| 4-47 | — | 1-[OPO(OPh)₂]Et | 1,2-diNH₂cHx |
| 4-48 | — | 1-AcOEt | 1,2-diNH₂cHx |
| 4-49 | — | 1-PrnOEt | 1,2-diNH₂cHx |
| 4-50 | — | 1-ByrOEt | 1,2-diNH₂cHx |
| 4-51 | — | 1-VaOEt | 1,2-diNH₂cHx |
| 4-52 | — | 1-HxoOEt | 1,2-diNH₂cHx |
| 4-53 | — | 1-HpoOEt | 1,2-diNH₂cHx |
| 4-54 | — | 1-(OctoO)Et | 1,2-diNH₂cHx |
| 4-55 | — | 1-BzOEt | 1,2-diNH₂cHx |
| 4-56 | — | 1-(MeOAcO)Et | 1,2-diNH₂cHx |
| 4-57 | — | 1-(PhOAcO)Et | 1,2-diNH₂cHx |
| 4-58 | — | 1-(PhAcO)Et | 1,2-diNH₂cHx |
| 4-59 | — | 1-MeOEt | 1,2-diNH₂cHx |
| 4-60 | — | 1-(MeOMeO)Et | 1,2-diNH₂cHx |
| 4-61 | — | 1-[MeOEtOMeO]Et | 1,2-diNH₂cHx |
| 4-62 | — | 1-MesOEt | 1,2-diNH₂cHx |
| 4-63 | — | 1-BesOEt | 1,2-diNH₂cHx |
| 4-64 | $CH_2$ | 1-HOEt | 1,2-diNH₂cHx |
| 4-65 | $CH_2$ | 1-(OSiMe₃)Et | 1,2-diNH₂cHx |
| 4-66 | $CH_2$ | 1-(OSiMe₂tBu)Et | 1,2-diNH₂cHx |
| 4-67 | $CH_2$ | 1-[OPO(OEt)₂]Et | 1,2-diNH₂cHx |
| 4-68 | $CH_2$ | 1-[OPO(OPh)₂]Et | 1,2-diNH₂cHx |
| 4-69 | $CH_2$ | 1-AcOEt | 1,2-diNH₂cHx |
| 4-70 | $CH_2$ | 1-PrnOEt | 1,2-diNH₂cHx |
| 4-71 | $CH_2$ | 1-ByrOEt | 1,2-diNH₂cHx |
| 4-72 | $CH_2$ | 1-VaOEt | 1,2-diNH₂cHx |
| 4-73 | $CH_2$ | 1-HxoOEt | 1,2-diNH₂cHx |
| 4-74 | $CH_2$ | 1-HpoOEt | 1,2-diNH₂cHx |
| 4-75 | $CH_2$ | 1-(OctoO)Et | 1,2-diNH₂cHx |
| 4-76 | $CH_2$ | 1-BzOEt | 1,2-diNH₂cHx |
| 4-77 | $CH_2$ | 1-(MeOAcO)Et | 1,2-diNH₂cHx |
| 4-78 | $CH_2$ | 1-(PhOAcO)Et | 1,2-diNH₂cHx |
| 4-79 | $CH_2$ | 1-(PhAcO)Et | 1,2-diNH₂cHx |
| 4-80 | $CH_2$ | 1-MeOEt | 1,2-diNH₂cHx |
| 4-81 | $CH_2$ | 1-(MeOMeO)Et | 1,2-diNH₂cHx |
| 4-82 | $CH_2$ | 1-[MeOEtOMeO]Et | 1,2-diNH₂cHx |
| 4-83 | $CH_2$ | 1-MesOEt | 1,2-diNH₂cHx |
| 4-84 | $CH_2$ | 1-BesOEt | 1,2-diNH₂cHx |
| 4-85 | — | 1-HOEt | 1-NH₂-2-NH₂MecHx |
| 4-86 | — | 1-(OSiMe₃)Et | 1-NH₂-2-NH₂MecHx |
| 4-87 | — | 1-(OSiMe₂tBu)Et | 1-NH₂-2-NH₂MecHx |
| 4-88 | — | 1-[OPO(OEt)₂]Et | 1-NH₂-2-NH₂MecHx |
| 4-89 | — | 1-[OPO(OPh)₂]Et | 1-NH₂-2-NH₂MecHx |
| 4-90 | — | 1-AcOEt | 1-NH₂-2-NH₂MecHx |
| 4-91 | — | 1-PrnOEt | 1-NH₂-2-NH₂MecHx |
| 4-92 | — | 1-ByrOEt | 1-NH₂-2-NH₂MecHx |
| 4-93 | — | 1-VaOEt | 1-NH₂-2-NH₂MecHx |
| 4-94 | — | 1-HxoOEt | 1-NH₂-2-NH₂MecHx |
| 4-95 | — | 1-HpoOEt | 1-NH₂-2-NH₂MecHx |
| 4-96 | — | 1-(OctoO)Et | 1-NH₂-2-NH₂MecHx |
| 4-97 | — | 1-BzOEt | 1-NH₂-2-NH₂MecHx |
| 4-98 | — | 1-(MeOAcO)Et | 1-NH₂-2-NH₂MecHx |
| 4-99 | — | 1-(PhOAcO)Et | 1-NH₂-2-NH₂MecHx |
| 4-100 | — | 1-(PhAcO)Et | 1-NH₂-2-NH₂MecHx |
| 4-101 | — | 1-MeOEt | 1-NH₂-2-NH₂MecHx |
| 4-102 | — | 1-(MeOMeO)Et | 1-NH₂-2-NH₂MecHx |
| 4-103 | — | 1-[MeOEtOMeO]Et | 1-NH₂-2-NH₂MecHx |
| 4-104 | — | 1-MesOEt | 1-NH₂-2-NH₂MecHx |
| 4-105 | — | 1-BesOEt | 1-NH₂-2-NH₂MecHx |
| 4-106 | $CH_2$ | 1-HOEt | 1-NH₂-2-NH₂MecHx |
| 4-107 | $CH_2$ | 1-(OSiMe₃)Et | 1-NH₂-2-NH₂MecHx |
| 4-108 | $CH_2$ | 1-(OSiMe₂tBu)Et | 1-NH₂-2-NH₂MecHx |
| 4-109 | $CH_2$ | 1-[OPO(OEt)₂]Et | 1-NH₂-2-NH₂MecHx |
| 4-110 | $CH_2$ | 1-[OPO(OPh)₂]Et | 1-NH₂-2-NH₂MecHx |
| 4-111 | $CH_2$ | 1-AcOEt | 1-NH₂-2-NH₂MecHx |
| 4-112 | $CH_2$ | 1-PrnOEt | 1-NH₂-2-NH₂MecHx |
| 4-113 | $CH_2$ | 1-ByrOEt | 1-NH₂-2-NH₂MecHx |
| 4-114 | $CH_2$ | 1-VaOEt | 1-NH₂-2-NH₂MecHx |
| 4-115 | $CH_2$ | 1-HxoOEt | 1-NH₂-2-NH₂MecHx |
| 4-116 | $CH_2$ | 1-HpoOEt | 1-NH₂-2-NH₂MecHx |
| 4-117 | $CH_2$ | 1-(OctoO)Et | 1-NH₂-2-NH₂MecHx |
| 4-118 | $CH_2$ | 1-BzOEt | 1-NH₂-2-NH₂MecHx |
| 4-119 | $CH_2$ | 1-(MeOAcO)Et | 1-NH₂-2-NH₂MecHx |
| 4-120 | $CH_2$ | 1-(PhOAcO)Et | 1-NH₂-2-NH₂MecHx |
| 4-121 | $CH_2$ | 1-(PhAcO)Et | 1-NH₂-2-NH₂MecHx |
| 4-122 | $CH_2$ | 1-MeOEt | 1-NH₂-2-NH₂MecHx |
| 4-123 | $CH_2$ | 1-(MeOMeO)Et | 1-NH₂-2-NH₂MecHx |
| 4-124 | $CH_2$ | 1-[MeOEtOMeO]Et | 1-NH₂-2-NH₂MecHx |
| 4-125 | $CH_2$ | 1-MesOEt | 1-NH₂-2-NH₂MecHx |
| 4-126 | $CH_2$ | 1-BesOEt | 1-NH₂-2-NH₂MecHx |
| 4-127 | — | 1-HOEt | 2-NH₂MePyrd |
| 4-128 | — | 1-(OSiMe₃)Et | 2-NH₂MePyrd |
| 4-129 | — | 1-(OSiMe₂tBu)Et | 2-NH₂MePyrd |
| 4-130 | — | 1-[OPO(OEt)₂]Et | 2-NH₂MePyrd |
| 4-131 | — | 1-[OPO(OPh)₂]Et | 2-NH₂MePyrd |
| 4-132 | — | 1-AcOEt | 2-NH₂MePyrd |
| 4-133 | — | 1-PrnOEt | 2-NH₂MePyrd |
| 4-134 | — | 1-ByrOEt | 2-NH₂MePyrd |
| 4-135 | — | 1-VaOEt | 2-NH₂MePyrd |
| 4-136 | — | 1-HxoOEt | 2-NH₂MePyrd |
| 4-137 | — | 1-HpoOEt | 2-NH₂MePyrd |
| 4-138 | — | 1-(OctoO)Et | 2-NH₂MePyrd |
| 4-139 | — | 1-BzOEt | 2-NH₂MePyrd |
| 4-140 | — | 1-(MeOAcO)Et | 2-NH₂MePyrd |
| 4-141 | — | 1-(PhOAcO)Et | 2-NH₂MePyrd |
| 4-142 | — | 1-(PhAcO)Et | 2-NH₂MePyrd |
| 4-143 | — | 1-MeOEt | 2-NH₂MePyrd |
| 4-144 | — | 1-(MeOMeO)Et | 2-NH₂MePyrd |
| 4-145 | — | 1-[MeOEtOMeO]Et | 2-NH₂MePyrd |
| 4-146 | — | 1-MesOEt | 2-NH₂MePyrd |
| 4-147 | — | 1-BesOEt | 2-NH₂MePyrd |
| 4-148 | $CH_2$ | 1-HOEt | 2-NH₂MePyrd |
| 4-149 | $CH_2$ | 1-(OSiMe₃)Et | 2-NH₂MePyrd |
| 4-150 | $CH_2$ | 1-(OSiMe₂tBu)Et | 2-NH₂MePyrd |
| 4-151 | $CH_2$ | 1-[OPO(OEt)₂]Et | 2-NH₂MePyrd |
| 4-152 | $CH_2$ | 1-[OPO(OPh)₂]Et | 2-NH₂MePyrd |
| 4-153 | $CH_2$ | 1-AcOEt | 2-NH₂MePyrd |
| 4-154 | $CH_2$ | 1-PrnOEt | 2-NH₂MePyrd |
| 4-155 | $CH_2$ | 1-ByrOEt | 2-NH₂MePyrd |

TABLE 4-continued

| Cpd No. | X | R¹ | A² |
|---|---|---|---|
| 4-156 | CH₂ | 1-VaOEt | 2-NH₂MePyrd |
| 4-157 | CH₂ | 1-HxoOEt | 2-NH₂MePyrd |
| 4-158 | CH₂ | 1-HpoOEt | 2-NH₂MePyrd |
| 4-159 | CH₂ | 1-(OctoO)Et | 2-NH₂MePyrd |
| 4-160 | CH₂ | 1-BzOEt | 2-NH₂MePyrd |
| 4-161 | CH₂ | 1-(MeOAcO)Et | 2-NH₂MePyrd |
| 4-162 | CH₂ | 1-(PhOAcO)Et | 2-NH₂MePyrd |
| 4-163 | CH₂ | 1-(PhAcO)Et | 2-NH₂MePyrd |
| 4-164 | CH₂ | 1-MeOEt | 2-NH₂MePyrd |
| 4-165 | CH₂ | 1-(MeOMeO)Et | 2-NH₂MePyrd |
| 4-166 | CH₂ | 1-[MeOEtOMeO]Et | 2-NH₂MePyrd |
| 4-167 | CH₂ | 1-MesOEt | 2-NH₂MePyrd |
| 4-168 | CH₂ | 1-BesOEt | 2-NH₂MePyrd |
| 4-169 | — | 1-HOEt | 1,2-diNH₂cOc |
| 4-170 | — | 1-(OSiMe₃)Et | 1,2-diNH₂cOc |
| 4-171 | — | 1-(OSiMe₂tBu)Et | 1,2-diNH₂cOc |
| 4-172 | — | 1-[OPO(OEt)₂]Et | 1,2-diNH₂cOc |
| 4-173 | — | 1-[OPO(OPh)₂]Et | 1,2-diNH₂cOc |
| 4-174 | — | 1-AcOEt | 1,2-diNH₂cOc |
| 4-175 | — | 1-PrnOEt | 1,2-diNH₂cOc |
| 4-176 | — | 1-ByrOEt | 1,2-diNH₂cOc |
| 4-177 | — | 1-VaOEt | 1,2-diNH₂cOc |
| 4-178 | — | 1-HxoOEt | 1,2-diNH₂cOc |
| 4-179 | — | 1-HpoOEt | 1,2-diNH₂cOc |
| 4-180 | — | 1-(OctoO)Et | 1,2-diNH₂cOc |
| 4-181 | — | 1-BzOEt | 1,2-diNH₂cOc |
| 4-182 | — | 1-(MeOAcO)Et | 1,2-diNH₂cOc |
| 4-183 | — | 1-(PhOAcO)Et | 1,2-diNH₂cOc |
| 4-184 | — | 1-(PhAcO)Et | 1,2-diNH₂cOc |
| 4-185 | — | 1-MeOEt | 1,2-diNH₂cOc |
| 4-186 | — | 1-(MeOMeO)Et | 1,2-diNH₂cOc |
| 4-187 | — | 1-[MeOEtOMeO]Et | 1,2-diNH₂cOc |
| 4-188 | — | 1-MesOEt | 1,2-diNH₂cOc |
| 4-189 | — | 1-BesOEt | 1,2-diNH₂cOc |
| 4-190 | CH₂ | 1-HOEt | 1,2-diNH₂cOc |
| 4-191 | CH₂ | 1-(OSiMe₃)Et | 1,2-diNH₂cOc |
| 4-192 | CH₂ | 1-(OSiMe₂tBu)Et | 1,2-diNH₂cOc |
| 4-193 | CH₂ | 1-[OPO(OEt)₂]Et | 1,2-diNH₂cOc |
| 4-194 | CH₂ | 1-[OPO(OPh)₂]Et | 1,2-diNH₂cOc |
| 4-195 | CH₂ | 1-AcOEt | 1,2-diNH₂cOc |
| 4-196 | CH₂ | 1-PrnOEt | 1,2-diNH₂cOc |
| 4-197 | CH₂ | 1-ByrOEt | 1,2-diNH₂cOc |
| 4-198 | CH₂ | 1-VaOEt | 1,2-diNH₂cOc |
| 4-199 | CH₂ | 1-HxoOEt | 1,2-diNH₂cOc |
| 4-200 | CH₂ | 1-HpoOEt | 1,2-diNH₂cOc |
| 4-201 | CH₂ | 1-(OctoO)Et | 1,2-diNH₂cOc |
| 4-202 | CH₂ | 1-BzOEt | 1,2-diNH₂cOc |
| 4-203 | CH₂ | 1-(MeOAcO)Et | 1,2-diNH₂cOc |
| 4-204 | CH₂ | 1-(PhOAcO)Et | 1,2-diNH₂cOc |
| 4-205 | CH₂ | 1-(PhAcO)Et | 1,2-diNH₂cOc |
| 4-206 | CH₂ | 1-MeOEt | 1,2-diNH₂cOc |
| 4-207 | CH₂ | 1-(MeOMeO)Et | 1,2-diNH₂cOc |
| 4-208 | CH₂ | 1-[MeOEtOMeO]Et | 1,2-diNH₂cOc |
| 4-209 | CH₂ | 1-MesOEt | 1,2-diNH₂cOc |
| 4-210 | CH₂ | 1-BesOEt | 1,2-diNH₂cOc |
| 4-211 | >CHMe | 1-HOEt | 1,2-diNH₂cHx |
| 4-212 | >CHMe | 1-(OSiMe₃)Et | 1,2-diNH₂cHx |
| 4-213 | >CHMe | 1-(OSiMe₂tBu)Et | 1,2-diNH₂cHx |
| 4-214 | >CHMe | 1-[OPO(OEt)₂]Et | 1,2-diNH₂cHx |
| 4-215 | >CHMe | 1-[OPO(OPh)₂]Et | 1,2-diNH₂cHx |
| 4-216 | >CHMe | 1-AcOEt | 1,2-diNH₂cHx |
| 4-217 | >CHMe | 1-PrnOEt | 1,2-diNH₂cHx |
| 4-218 | >CHMe | 1-ByrOEt | 1,2-diNH₂cHx |
| 4-219 | >CHMe | 1-VaOEt | 1,2-diNH₂cHx |
| 4-220 | >CHMe | 1-HxoOEt | 1,2-diNH₂cHx |
| 4-221 | >CHMe | 1-HpoOEt | 1,2-diNH₂cHx |
| 4-222 | >CHMe | 1-(OctoO)Et | 1,2-diNH₂cHx |
| 4-223 | >CHMe | 1-BzOEt | 1,2-diNH₂cHx |
| 4-224 | >CHMe | 1-(MeOAcO)Et | 1,2-diNH₂cHx |
| 4-225 | >CHMe | 1-(PhOAcO)Et | 1,2-diNH₂cHx |
| 4-226 | >CHMe | 1-(PhAcO)Et | 1,2-diNH₂cHx |
| 4-227 | >CHMe | 1-MeOEt | 1,2-diNH₂cHx |
| 4-228 | >CHMe | 1-(MeOMeO)Et | 1,2-diNH₂cHx |
| 4-229 | >CHMe | 1-[MeOEtOMeO]Et | 1,2-diNH₂cHx |
| 4-230 | >CHMe | 1-MesOEt | 1,2-diNH₂cHx |
| 4-231 | >CHMe | 1-BesOEt | 1,2-diNH₂cHx |
| 4-232 | >CMe₂ | 1-HOEt | 1,2-diNH₂cHx |
| 4-233 | >CMe₂ | 1-(OSiMe₃)Et | 1,2-diNH₂cHx |
| 4-234 | >CMe₂ | 1-(OSiMe₂tBu)Et | 1,2-diNH₂cHx |
| 4-235 | >CMe₂ | 1-[OPO(OEt)₂]Et | 1,2-diNH₂cHx |
| 4-236 | >CMe₂ | 1-[OPO(OPh)₂]Et | 1,2-diNH₂cHx |
| 4-237 | >CMe₂ | 1-AcOEt | 1,2-diNH₂cHx |
| 4-238 | >CMe₂ | 1-PrnOEt | 1,2-diNH₂cHx |
| 4-239 | >CMe₂ | 1-ByrOEt | 1,2-diNH₂cHx |
| 4-240 | >CMe₂ | 1-VaOEt | 1,2-diNH₂cHx |
| 4-241 | >CMe₂ | 1-HxoOEt | 1,2-diNH₂cHx |
| 4-242 | >CMe₂ | 1-HpoOEt | 1,2-diNH₂cHx |
| 4-243 | >CMe₂ | 1-(OctoO)Et | 1,2-diNH₂cHx |
| 4-244 | >CMe₂ | 1-BzOEt | 1,2-diNH₂cHx |
| 4-245 | >CMe₂ | 1-(MeOAcO)Et | 1,2-diNH₂cHx |
| 4-246 | >CMe₂ | 1-(PhOAcO)Et | 1,2-diNH₂cHx |
| 4-247 | >CMe₂ | 1-(PhAcO)Et | 1,2-diNH₂cHx |
| 4-248 | >CMe₂ | 1-MeOEt | 1,2-diNH₂cHx |
| 4-249 | >CMe₂ | 1-(MeOMeO)Et | 1,2-diNH₂cHx |
| 4-250 | >CMe₂ | 1-[MeOEtOMeO]Et | 1,2-diNH₂cHx |
| 4-251 | >CMe₂ | 1-MesOEt | 1,2-diNH₂cHx |
| 4-252 | >CMe₂ | 1-BesOEt | 1,2-diNH₂cHx |

TABLE 5

| Cpd No. | X | R¹ | R⁷ |
|---|---|---|---|
| 5-1 | — | H | H |
| 5-2 | — | Me | H |
| 5-3 | — | MeO | H |
| 5-4 | — | Br | H |
| 5-5 | — | H | COOEt |
| 5-6 | — | Me | COOEt |
| 5-7 | — | MeO | COOEt |
| 5-8 | — | Br | COOEt |
| 5-9 | CH₂ | H | H |
| 5-10 | CH₂ | Me | H |
| 5-11 | CH₂ | MeO | H |
| 5-12 | CH₂ | Br | H |
| 5-13 | CH₂ | H | COOEt |
| 5-14 | CH₂ | Me | COOEt |
| 5-15 | CH₂ | MeO | COOEt |
| 5-16 | CH₂ | Br | COOEt |
| 5-17 | — | Et | CN |
| 5-18 | — | iPr | CN |
| 5-19 | CH₂ | Et | CN |
| 5-20 | CH₂ | iPr | CN |

Of the compounds listed above, the most preferred compounds are:

1,2-diaminocyclohexaneplatinum(II) 2-oxoazetidine-4,4-dicarboxylate, especially the cis-[trans-(l)-1,2-diaminocyclohexane]platinum(II) 2-oxoazetidine-4,4-dicarboxylate isomer;

1,2-diaminocyclohexaneplatinum(II) (1-methyl-2-oxoazetidine-4,4-dicarboxylate), especially the cis-[trans-(l)-1,2-diaminocyclohexane]platinum(II) (1-methyl-2-oxoazetidine-4,4-dicarboxylate) isomer;

1,2-diaminocyclohexaneplatinum(II) (1-methoxymethyl-2-oxoazetidine-4,4-dicarboxylate), especially the cis-[trans-(1)-1,2-diaminocyclohexane]platinum(II) (1-methoxymethyl-2-oxoazetidine-4,4-dicarboxylate) isomer;

1,2-diaminocyclohexaneplatinum(II) [1-(2-methoxyethoxy)methyl-2-oxoazetidine-4,4-dicarboxylate], especially the cis-[trans-(l)-1,2-diaminocyclohexane]platinum(II) [1-(2-methoxyethoxy)methyl-2-oxoazetidine-4,4-dicarboxylate] isomer;

1,2-diaminocyclohexaneplatinum(II) (1-methyl-3-isopropyl-2-oxoazetidine-4,4-dicarboxylate), especially the cis-[trans-(l)-1,2-diaminocyclohexane]platinum(II) (1-methyl-3-isopropyl-2-oxoazetidine-4,4-dicarboxylate) isomer;

1,2-diaminocyclohexaneplatinum(II) 3-[1-(methoxymethoxy)ethyl]-2-oxoazetidin-4-ylacetate, especially the cis-[trans-(l)-1,2-diaminocyclohexane] platinum(II) {(3S, 4R)-3-[(R)-1-(methoxymethoxy)ethyl]-2-oxoazetidin-4-yl}acetate isomer;

1,2-diaminocyclohexaneplatinum(II) 3-[1-(2-methoxyethoxymethoxy)ethyl]-2-oxoazetidin-4-ylacetate, especially the cis-[trans-(l)-1,2-diaminocyclohexane]platinum(II) {(3S, 4R)-3-[(R)-1-(2-methoxyethoxymethoxy)ethyl]-2-oxoazetidin-4-yl}acetate isomer;

1,2-diaminocyclohexaneplatinum(II) 3-(1-octanoyloxyethyl)-2-oxoazetidin-4-ylcarboxylate, especially the cis-[trans-(l)-1,2-diaminocyclohexane]platinum (II) {(3S, 4S)-3-[(R)-1-octanoyloxyethyl]-2-oxoazetidin-4-yl}carboxylate isomer; and 1,2-diaminocyclohexaneplatinum(II) 3-(1-t-butyldimethylsilyloxyethyl)-2-oxoazetidin-4-ylcarboxylate, especially the cis-[trans-(l)-1,2-diaminocyclohexane]platinum(II) {(3S, 4S)-3-[(R)-1-t-butyldimethylsilyloxyethyl]-2-oxoazetidin-4-yl}carboxylate isomer.

The compounds of the present invention can be prepared by a variety of methods well known for preparing this type of complex. Examples of suitable preparative procedures are illustrated in the following reaction schemes:

Reaction Scheme A1

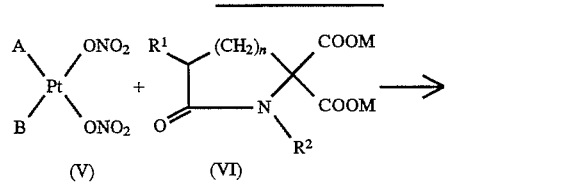

Reaction Scheme A2

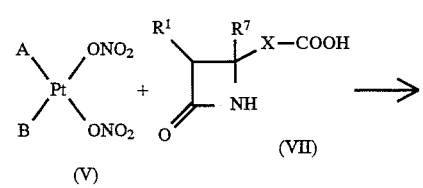

Reaction Scheme A2

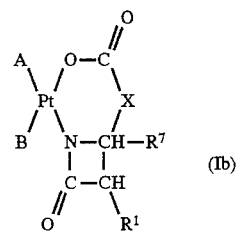

Reaction Scheme B1

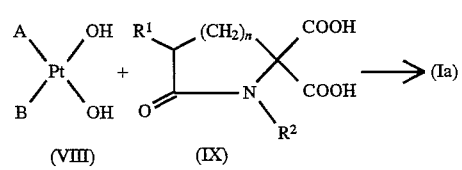

Reaction Scheme B2

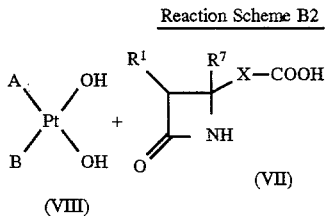

In the above formulae, A, B, $R^1$, $R^2$, $R^7$, X and n are as defined above. M represents an atom of a metal capable of generating an alkaline medium, for example an alkali metal, especially sodium or potassium.

The platinum complexes of formulae (V) and (VIII), used as starting materials are well known compounds. The mono- and di-carboxylic acids of formulae (VII) and (IX) and the salt of formula (VI) can be prepared as described in Japanese Patent Application Kokai No. 56-142259.

In Reaction Scheme A1, the compound of formula (V) is reacted with the compound of formula (VI), to give the desired compound of formula (Ia). This reaction is preferably effected by adding the salt of formula (VI), preferably in an equivalent amount or in a slight molar excess, to the complex of formula (V), preferably in an aqueous solution or aqueous suspension. In Reaction Scheme A2, the compound of formula (V) is reacted with the compound of formula (VII), to give the desired compound of formula (Ib). This reaction is preferably effected by adding the acid of formula (VII), preferably in an equivalent amount or in a slight molar excess, and an alkali (e.g. an alkali metal hydroxide, such as sodium hydroxide or potassium hydroxide, or an alkaline resin), preferably in an amount of about 2 equivalents, to the complex of formula (V), preferably in an aqueous solution or aqueous suspension. Alternatively, the process of Reaction Scheme A1 may be carried out using the acid corresponding to the salt of formula (VI) in the presence of such an alkali, or the process of Reaction Scheme A2 may be carried out using the salt corresponding to the acid of formula (VII) without necessarily employing any added alkali.

Both reactions are preferably carried out at a temperature of from 0° C. to 50° C., although the reaction temperature is not too critical to the present invention. The time required for the reaction may vary widely, depending on many factors, notably the reaction temperature and the nature of the reagents; however, a period of from 20 minutes to 5 days will normally suffice for Reaction Scheme A1 and a period of from 20 minutes to 20 days will normally suffice for Reaction Scheme A2.

When the reaction is deemed to be complete, the resulting precipitate may usually be collected by filtration. However, if the desired compound does not precipitate as crystals, the compound may be recovered by the following recovery sequence: first the reaction mixture is concentrated by evaporation under reduced pressure; the residue is mixed with a solvent which has no adverse effect on the desired compound; this may cause the desired compound to crystallise out—if so, it may be collected by filtration; alternatively, the resulting solution may be purified by one of the various chromatography techniques, such as column chromatography, e.g. using an adsorptive resin, such as Diaion (trade mark) CHP-20P or Sephadex (trade mark), or an ion-exchange resin, to give the desired compound.

The complex of formula (VIII) used as a starting material in Reaction Schemes B1 and B2, may be prepared by treating the complex of formula (V) with an alkali (e.g. an alkali metal hydroxide, such as sodium hydroxide or potassium hydroxide, or an alkaline resin). This can then be reacted with the compound of formula (IX) or (VII), in a similar manner to that described with reference to Reaction Schemes A1 and A2.

The compounds of the present invention have shown excellent anti-tumor activity which is comparable with or better than that of cisplatin and carboplatin. Moreover, quite unexpectedly, it has been found that the compounds of the invention are even effective against a cisplatin-resistant strain of mouse leukemia L1210. Moreover, the compounds of the invention appear to have surprisingly limited side-effects, such as renal toxicity and bone marrow suppression, and they have a very high solubility in water, which makes them very easy to administer. The strains of tumor against which the compounds have been tested are recognised as providing a model for assessing the likely value of a compound for the treatment of tumors affecting human beings.

There is no particular restriction on the route of administration, but, for use as a carcinostatic agent, the platinum complexes of the present invention are preferably administered parenterally, for example as injections. The dosage may vary depending upon the age, body weight and condition of the patient, as well as the nature and severity of the tumor, but we generally prefer to administer the compound in an amount of from 10 mg to several grams per day for adult human patients, generally as divided doses.

The invention is further illustrated with reference to the following non-limiting Examples. Preparation of certain of the starting materials used in these Examples is illustrated by the subsequent Preparations. The subsequent Experiment illustrates the biological activity of certain of the compounds of the present invention.

EXAMPLE 1 cis-[trans-(l)-1,2-Diaminocyclohexane]platinum(II) 2-oxoazetidine-4,4-dicarboxylate 2 g of cis-[trans-(l)-1,2-diaminocyclohexane]platinum(II) dinitrate were suspended in 80 ml of water, and the suspension was stirred at 28° C. overnight. At the end of this time, the reaction mixture was concentrated by evaporation under reduced pressure to a volume of about 45 ml, and then 1 g of sodium 2-oxoazetidine-4,4-dicarboxylate (prepared as described in Preparation 1) was added to the concentrate. The mixture was then adjusted to a pH value of 6.1 by adding an aqueous solution of sodium hydroxide and was stirred for about 2 hours, whilst ice-cooling. The precipitated crystals were collected by filtration and washed with small amounts of water and of diethyl ether to give 0.58 g of the title compound.

Nuclear Magnetic Resonance Spectrum (270 MHz, $D_2O$) δ ppm:

0.9–1.1 (4H, multiplet);

1.3–1.45 (2H, doublet-like);

1.8–1.9 (2H, doublet-like);

2.1–2.3 (2H, multiplet);

3.74 (2H, singlet),

EXAMPLE 2 cis-Diammineplatinum(II) 2-oxoazetidine-4,4-dicarboxylate

A solution of 200 mg of sodium 2-oxoazetidine-4,4-dicarboxylate (prepared as described in Preparation 1) in 5 ml of water was added to a suspension of 347 mg of cis-diammineplatinum(II) dinitrate in 5 ml of water, and the mixture was stirred at room temperature overnight. At the end of this time, the precipitated crystals were collected by filtration and washed with small amounts of water and of diethyl ether, to give 19 mg of the title compound, which was further purified by recrystallization from water.

Nuclear Magnetic Resonance Spectrum (270 MHz, $D_2O$) δ ppm: 3.76 (2H, singlet).

EXAMPLE 3 cis-[trans-(l)-1,2-Diaminocyclohexane]platinum(II) (1-methyl-2-oxoazetidine-4,4-dicarboxylate)

Following a procedure similar to that described in Example 1, 0.09 g of the title compound was prepared from 0.399 g of cis-[trans-(l)-1,2-diaminocyclohexane]-platinum (II) dinitrate and 0.2 g of sodium 1-methyl-2-oxoazetidine-4,4-dicarboxylate (prepared as described in Preparation 1).

Nuclear Magnetic Resonance Spectrum (270 MHz, $D_2O$) δ ppm:

0.9–1.2 (4H, multiplet);

1.4 (2H, doublet-like);

1.85 (2H, doublet-like);

2.2 (2H, broad singlet-like);

2.80 (3H, singlet);

3.63 (2H, singlet).

EXAMPLE 4 cis-[trans-(l)-1,2-Diaminocyclohexane]platinum(II) (1,3-dimethyl-2-oxoazetidine-4,4-dicarboxylate)

A solution of 0.2 g of 1,3-dimethyl-2-oxoazetidine- 4,4-dicarboxylic acid in 5 ml of water was added to a solution of 0.3 g of cis-[trans-(l)-1,2-diaminocyclohexane] dihydroxyplatinum(II) dissolved in 10 ml of water. The mixture was then stirred at room temperature for 5 hours. At the end of this time, the water was stripped from the mixture by evaporation under reduced pressure, and the residue was mixed with acetone to induce crystallization. The resulting crystals were collected by filtration and washed with acetone to yield 0.31 g of a crude title compound. This was dissolved in water and purified by column chromatography through a column containing Sephadex LH-20 (eluted with water) to give 0.17 g of the title compound.

Nuclear Magnetic Resonance Spectrum (270 MHz, $D_2O$) δ ppm:

0.9–1.2 (4H, multiplet);
1.38 (2H, doublet-like);
1.54 and 1.59 (together 3H, each doublet, J=7 Hz);
1.85 (2H, doublet-like);
2.74 and 2.75 (together 3H, each singlet);
3.61 and 3.64 (together 1H, each quartet, J=7 Hz).

EXAMPLE 5 cis-[trans-(l)-1,2-Diaminocyclohexane]platinum(II) 2-oxopyrrolidine-5,5-dicarboxylate 440 mg of sodium 2-oxopyrrolidine-5,5-dicarboxylate (prepared as described in Preparation 2) were added to a solution of 866 mg of cis-[trans-(l)-1,2-diaminocyclohexane]platinum(II) dinitrate in 70 ml of water, and the mixture was kept at 26° C. for 7 hours. At the end of this time, the precipitated crystals were collected by filtration and washed with water, to give 219 mg of the title compound as colorless crystals. The filtrate was then concentrated to a volume of 40 ml by evaporation under reduced pressure and allowed to stand at 26° C. The resulting crystals were then treated in a similar manner to that described above to give a further 170 mg of the title compound.

Nuclear Magnetic Resonance Spectrum (270 MHz, $D_2O$) δ ppm:

0.87–1.23 (4H, multiplet):
1.32–1.48 (2H, multiplet);
1.81–1.95 (2H, multiplet);
2.15–2.30 (2H, multiplet);
2.31 (2H, triplet, J=7.9 Hz);
3.14–3.32 (2H, multiplet).

Infrared Absorption Spectrum (KBr) $v_{max}$ $cm^{-1}$: 1709, 1671, 1630.

EXAMPLE 6 cis-[trans-(l)-1,2-Diaminocyclohexane]platinum (II) (3-isopropyl-2-oxoazetidine-4,4-dicarboxylate)

Following a procedure similar to that described in Example 1, 260 mg of the title compound were prepared from 707 mg of cis-(trans-(l)-1,2-diaminocyclohexane) platinum (II) dinitrate and 400 mg of 3-isopropyl-2-oxoazetidine-4,4-dicarboxylate.

Nuclear Magnetic Resonance Spectrum (270 MHz, $D_2O$) δ ppm:

0.79 (3H, doublet, J=6.6 Hz);
0.9–1.05 (2H, multiplet);
1.0–1.2 (2H, multiplet);
1.16 (3H, doublet, J=7 Hz);
1.3–1.45 (2H, multiplet);
1.8–1.9 (2H, multiplet);
2.1–2.35 (2H, multiplet);
2.76 (3H, singlet);
3.05–3.2 (1H, multiplet);
3.47 (1H, doublet, J=3.3 Hz).

EXAMPLE 7 cis-[trans-(l)-1,2-Diaminocyclohexane]platinum (II) (1-methyl-3-isopropyl-2-oxoazetidine-4,4-dicarboxylate)

Following a procedure similar to that described in Example 1, 660 mg of the title compound were prepared from 1.3 g of cis-[trans-(l)-1,2-diaminocyclohexane] platinum (II) dinitrate and 780 mg of sodium 1-methyl-3-isopropyl-2-oxoazetidine-4,4-dicarboxylate.

Nuclear Magnetic Resonance Spectrum (270 MHz, $D_2O$) δ ppm:

0.81 (3H, doublet, J=7 Hz);
0.9–1.2 (4H, multiplet);
1.18 (3H, doublet, J=7 Hz);
1.35–1.45 (2H, multiplet);
1.8–1.95 (2H, multiplet);
2.05–2.3 (2H, multiplet);
2.76 (3H, singlet);
3.05–3.2 (1H, multiplet);
3.51 (1H, doublet, J=4 Hz).

EXAMPLE 8 cis-[trans-(l)-1,2-Diaminocyclohexane]platinum (II) (1-methoxymethyl-2-oxoazetidine-4,4-dicarboxylate)

Following a procedure similar to that described in Example 1, 200 mg of the title compound were prepared from 500 mg of cis-[trans-(l)-1,2-diaminocyclohexane] platinum (II) dinitrate and 280 mg of sodium 1-methoxymethyl-2-oxoazetidine-4,4-dicarboxylate.

Nuclear Magnetic Resonance Spectrum (270 MHz, $D_2O$) δ ppm:

0.85–1.2 (4H, multiplet);
1.3–1.45 (2H, multiplet);
1.8–1.9 (2H, multiplet);
2.1–2.3 (2H, multiplet);
3.24 (3H, singlet);
3.76 (2H, singlet);
4.57 (2H, singlet).

EXAMPLE 9 cis-[trans-(l)-1,2-Diaminocyclohexane]platinum (II) [1-(2-methoxyethoxy)methyl-2-oxoazetidine-4,4-dicarboxylate]

Following a procedure similar to that described in Example 1, 135 mg of the title compound were prepared from 300 mg of cis-[trans-(l)-1,2-diaminocyclohexane] platinum (II) dinitrate and 200 mg of sodium 1-(2-methoxyethoxy)methyl-2-oxoazetidine-4,4-dicarboxylate.

Nuclear Magnetic Resonance Spectrum (270 MHz, $D_2O$) δ ppm:

0.9–1.2 (4H, multiplet);
1.35–1.45 (2H, multiplet);
1.8–1.9 (2H, multiplet);
2.15–2.3 (2H, multiplet);
3.19 (3H, singlet);
3.4–3.47 (2H, multiplet);
3.6–3.65 (2H, multiplet);

3.76 (2H, singlet);
4.66 (2H, singlet).

EXAMPLE 10 cis-[trans-(l)-1,2-Diaminocyclohexane]Platinum (II) (1-methoxymethyl-3-isopropyl-2-oxoazetidine-4,4-dicarboxylate)

Following a procedure similar to that described in Example 1, 630 mg of the title compound were prepared from 750 mg of cis-[trans-(l)-1,2-diaminocyclohexane] platinum (II) dinitrate and 500 mg of sodium 1-methoxymethyl-3-isopropyl-2-oxoazetidine-4,4-dicarboxylate.

Nuclear Magnetic Resonance Spectrum (270 MHz, $D_2O$) δ ppm:

0.81 (3H, doublet, J=5.5 Hz);
0.9–1.25 (4H, multiplet);
1.16 (3H, doublet, J=7 Hz);
1.3–1.45 (2H, multiplet);
1.8–1.9 (2H, multiplet);
2.1–2.35 (2H, multiplet);
3.23 (3H, singlet);
3.1–3.3 (1H, multiplet);
3.58 (1H, doublet, J=3.3 Hz);
4.45 (1H, doublet, J=12 Hz);
4.62 (1H, doublet, J=12 Hz).

EXAMPLE 11 cis-[trans-(d)-1,2-Diaminocyclohexane]platinum (II) 2-oxoazetidine-4,4-dicarboxylate Following a procedure similar to that described in Example 1, 125 mg of the title compound were prepared from 500 mg of cis-[trans-(l)-1,2-diaminocyclohexane] platinum (II) dinitrate and 234 mg of sodium 2-oxoazetidine-4,4-dicarboxylate.

Nuclear Magnetic Resonance Spectrum (270 MHz, $D_2O$) δ ppm:

0.9–1.1 (4H, multiplet);
1.3–1.45 (2H, doublet-like);
1.8–1.9 (2H, doublet-like);
2.1–2.3 (2H, multiplet);
3.74 (2H, singlet).

EXAMPLE 12 cis-Diammineplatinum (II) (1-methyl-3-isopropyl-2-oxoazetidine-4,4-dicarboxylate)

Following a procedure similar to that described in Example 2, 200 mg of the title compound were prepared from 400 mg of cis-diammineplatinum (II) dinitrate and 300 mg of sodium 1-methyl-3-isopropyl-2-oxoazetidine-4,4-dicarboxylate.

Nuclear Magnetic Resonance Spectrum [270 MHz, $(CD_3)_2SO$] δ ppm:

0.88 (3H, doublet, J=6.3 Hz);
1.22 (3H, doublet, J=6.8 Hz);
2.81 (3H, singlet);
2.7–2.9 (1H, multiplet);
3.40 (1H, doublet, J=3 Hz);
4.2 (6H, broad singlet).

EXAMPLE 13 cis-Diammineplatinum (II) (1-methoxymethyl-2-oxoazetidine-4,4-dicarboxylate)

Following a procedure similar to that described in Example 2, 105 mg of the title compound were prepared from 200 mg of cis-diammineplatinum (II) dinitrate and 134 mg of sodium 1-methoxymethyl-2-oxozetidine-4,4-dicarboxylate.

Nuclear Magnetic Resonance Spectrum (270 MHz, $D_2O$) δ ppm:

3.31 (3H, singlet);
6.67 (2H, singlet);
4.24 (6H, broad singlet);
4.60 (2H, singlet).

EXAMPLE 14 cis-[trans-(l)-1,2-Diaminocyclohexane]platinum(II) {(3S, 4R)-3-[(R)-1-t-butyldimethylsilyloxyethyl]-2-oxoazetidin-4-yl}acetate 1.9 g of cis-[trans-(l)-1,2-diaminocyclohexane]platinum (II) dinitrate was suspended in 100 ml of water, and the suspension was stirred at 28° C. overnight. At the end of this time, a solution of (3S, 4R)-3-[(R)-1-t-butyldimethylsilyloxyethyl]-2-oxoazetidin-4-ylacetic acid dissolved in 2 equivalents of aqueous sodium hydroxide was added to the reaction mixture, and immediately crystals precipitated. These crystals were collected by filtration, washed with water and dried, to give 1.6 g of the title compound as a pale yellow powder.

Nuclear Magnetic Resonance Spectrum (270 MHz, $CD_3OD$) δ ppm:

0.09 (3H, singlet);
0.10 (3H, singlet);
0.90 (9H, singlet);
1.1–1.4 (2H, multiplet);
1.29 (3H, doublet, J=6.5 Hz);
1.5–1.8 (2H, multiplet);
1.9–2.2 (2H, multiplet);
2.2–2.4 (2H, multiplet);
2.45 (1H, doublet of doublets, J=14 & 10 Hz);
2.57 (1H, doublet of doublets, J=14 & 5.5 Hz);
2.86 (1H, doublet of doublets);
4.09 (1H, multiplet);
4.29 (1H, multiplet).

EXAMPLE 15 cis-[trans-(d)-1,2-Diaminocyclohexane]platinum(II) {(3S, 4R)-3-[(R)-1-t-butyldimethylsilyloxyethyl]-2-oxoazetidin-4-yl}acetate Following a procedure similar to that described in Example 14, 1.56 g of the title compound were prepared from 1.9 g of cis-[trans-(l)-1,2-diaminocyclohexane] platinum(II) dinitrate.

Nuclear Magnetic Resonance Spectrum (270 MHz, $CD_3OD$) δ ppm:

0.09 (3H, singlet);
0.10 (3H, singlet);
0.90 (9H, singlet);
1.1–1.4 (2H, multiplet);
1.23 (3H, doublet, J=6.3 Hz;
1.5–1.8 (2H, multiplet);
1.9–2.2 (2H, multiplet);
2.2–2.4 (2H, multiplet);
2.4–2.7 (2H, multiplet);
2.84 (1H, doublet of doublets);
4.01 (1H, multiplet);
4.21 (1H, multiplet).

EXAMPLE 16 cis-[trans-(l)-1,2-Diaminocyclohexane]platinum(II) {(3S, 4R)-3-[(R)-1-hydroxyethyl]-2-oxoazetidin-4-yl}acetate 866 mg of cis-[trans-(l)-1,2-diaminocyclohexane]platinum(II) dinitrate were suspended in 30 ml of water, and then 350 mg of (3S, 4R)-3-[(R)-1-hydroxyethyl]-2-oxoazetidin-4-ylacetic acid and 2 equivalents of a 1N aqueous solution of sodium hydroxide were added to the suspension. The mixture was then stirred at room temperature for 18 days. At the end of this time, the reaction mixture was concentrated by evaporation under reduced pressure, and the residue was purified by column chromatography through a column containing CHP-20P resin, eluted with water, to give 100 mg of the title compound as a colorless powder.

Nuclear Magnetic Resonance Spectrum (270 MHz, $D_2O$) δ ppm:

0.8–1.3 (4H, multiplet);
1.12 (3H, doublet, J=6.2 Hz);
1.3–1.5 (2H, multiplet);
1.8–2.0 (2H, multiplet);
2.1–2.5 (5H, multiplet);
3.48 (1H, multiplet);
4.5 (1H, multiplet).

EXAMPLE 17 cis-[trans-(l)-1,2-Diaminocyclohexane]platinum(II) {(3S, 4R)-3-[(R)-1-(methoxymethoxy)ethyl]-2-oxoazetidin-4-ylacetate Following a procedure similar to that described in Example 16, 64 mg of the title compound were prepared from 199 mg of cis-[trans-(l)-1,2-diaminocyclohexane]platinum(II) dinitrate and 100 mg of (3S, 4R)-3-[(R)-1-(methoxymethoxy)ethyl]-2-oxoazetidin-4-ylacetic acid.

Nuclear Magnetic Resonance Spectrum (270 MHz, $D_2O$) δ ppm:

0.9–1.1 (4H, multiplet);
1.07 (3H, doublet, J=6 Hz);
1.3–1.5 (2H, multiplet);
1.8–1.9 (2H, multiplet);
2.1–2.2 (2H, multiplet);
2.35 (1H, doublet of doublets, J=15 & 8 Hz);
2.41 (1H, doublet of doublets, J=15 & 6 Hz);
2.91 (1H, doublet of doublets, J=5, 2 Hz);
3.19 (3H, singlet);
3.76 (1H, doubled doublet of doublets, J=8, 6 & 2 Hz);
3.95 (1H, quartet, doublet, J=6 & 5 Hz).

EXAMPLE 18 cis-[trans-(l)-1,2-Diaminocyclohexane]platinum(II) {(3S, 4R)-3-[(R)-1-(2-methoxyethoxymethoxy)ethyl]-2-oxoazetidin-4-yl}acetate Following a procedure similar to that described in Example 16, 83 mg of the title compound were prepared from 166 mg of cis-[trans-(l)-1,2-diaminocyclohexane]platinum(II) dinitrate and 100 mg of (3S, 4R)-3-[(R)-1-(2-methoxyethoxymethoxy)ethyl]-2-oxoazetidin-4-ylacetic acid.

Nuclear Magnetic Resonance Spectrum (270 MHz, $D_2O$) δ ppm:

0.8–1.2 (4H, multiplet);
1.07 (3H, doublet, J=6.6 Hz);
1.3–1.5 (2H, multiplet);
1.7–1.9 (2H, multiplet);
2.1–2.2 (2H, multiplet);
2.35 (1H, doublet of doublets, J=15 & 8 Hz);
2.40 (1H, doublet of doublets, J=15 & 6 Hz);
2.91 (1H, doublet of doublets, J=4.4 & 1.8 Hz);
3.19 (3H, singlet);
~3.45 (2H, multiplet);
~3.54 (2H, multiplet);
3.75 (1H, doublet of triplets, J=2.2 & 5.8 Hz);
3.98 (1H, doublet of quartets).

EXAMPLE 19 cis-[trans-(l)-1,2-Diaminocyclohexane]platinum(II) {(3S, 4R)-3-[(R)-1-diethylphosphonoxyethyl]-2-oxoazetidin-4-yl}acetate Following a procedure similar to that described in Example 16, 27 mg of the title compound were prepared from 188 mg of cis-[trans-(l)-1,2-diaminocyclohexane]platinum(II) dinitrate and 150 mg of (3S, 4R)-3-[(R)-1-diethylphosphonoxyethyl]-2-oxoazetidin-4-ylacetic acid.

Nuclear Magnetic Resonance Spectrum (270 MHz, $D_2O$) δ ppm:

0.9–1.2 (4H, multiplet);
1.10 (4H, triplet of doublets, J=7, 20 Hz);
1.24 (3H, doublet, J=7 Hz);
1.3–1.5 (2H, multiplet);
1.8–1.9 (2H, multiplet);
2.1–2.2 (2H, multiplet);
2.37 (1H, doublet of doublets, J=7 & 14 Hz);
2.42 (1H, doublet of doublets, J=6 & 14 Hz);
3.02 (1H, doublet of doublets, J=2 & 6 Hz);
3.73 (1H, quintet, J=7 Hz);
3.86 (1H, doublet of triplets, J=2 & 6 Hz);
3.9–4.1 (4H, multiplet).

EXAMPLE 20 cis-[trans-(l)=1,2-Diaminocyclohexane]platinum(II) {(3S, 4R)-3-[(R)-1-diphenylphosphonoxyethyl]-2-oxoazetidin-4-yl}acetate Following a procedure similar to that described in Example 16, 101 mg of the title compound were prepared from 107 mg of cis-[trans-(l)-1,2-diaminocyclohexane] platinum(II) dinitrane and 100 mg of (3S, 4R)-3-[(R)-1-diphenylphosphonoxyethyl]-2-oxoazetidin-4-ylacetic acid.

Nuclear Magnetic Resonance Spectrum (270 MHz, $D_2O$) δ ppm:

0.8–1.2 (4H, multiplet);
1.27 (3H, doublet, J=6 Hz);
1.3–1.5 (2H, multiplet);
1.7–2.0 (2H, multiplet);
2.0–2.3 (2H, multiplet);
2.27 (2H, multiplet);
3.00 (1H, doublet of doublets, J=3 & 7 Hz);
3.73 (1H, doublet of triplets, J=2 & 8 Hz);
4.93 (1H, multiplet);
7.0–7.4 (10H, multiplet).

EXAMPLE 21 cis-[trans-(l)-1,2-Diaminocyclohexane]platinum(II) {(3S, 4S)-3-[(R)-1-t-butyldimethylsilyloxyethyl]-2-oxoazetidin-4-yl}carboxylate Following a procedure similar to that described in Example 14, 0.16 g of the title compound was prepared from 0.19 g of cis-[trans-(l)-1,2-diaminocyclohexane]platinum (II) dinitrate and 0.13 g of (3S, 4S)-3-[(R)-1-t-butyldimethylsilyloxyethyl]-2-oxoazetidine-4-carboxylic acid.

Nuclear Magnetic Resonance Spectrum (270 MHz, $CD_3OD$) δ ppm:

0.05 (3H, singlet);
0.09 (3H, singlet);
0.90 (9H, singlet);
1.1–1.4 (4H, multiplet);
1.29 (3H, doublet, J=7 Hz);
1.5–1.8 (2H, multiplet);
1.95–2.15 (2H, multiplet);
2.2–2.4 (2H, multiplet);
3.13 (1H, triplet, J=2 Hz);
4.10 (1H, doublet, J=2 Hz);
4.30 (1H, doublet of quartets, J=7.2 Hz).

EXAMPLE 22 cis-[trans-(l)-1,2-Diaminocyclohexane]platinum(II) {(3S, 4S)-3-[(R)-1-octanoyloxyethyl]-2-oxoazetidin-4-yl}carboxylate 228 mg of cis-[trans-(l)-1,2-diaminocyclohexane]platinum(II) dinitrate were suspended in 10 ml of water, and the suspension was stirred at 26° C. for 3 hours to form a homogeneous solution. At the end of this time, 1.05 ml of a 1N aqueous solution of sodium hydroxide and 150 mg of (3S, 4S)-3-[(R)-1-octanoyloxyethyl]-2-oxoazetidine-4-carboxylic acid were added to the solution, and the resulting mixture was then stirred at room temperature for 1.5 hours. The crystals which precipitated were collected by filtration and washed with water, acetone and diethyl ether, in that order, to afford 84 mg of the title compound. Further crystals precipitated from a mixture of the filtrate and the water washings after the mixture had been allowed to stand for 2 days at room temperature. The resulting crystals were collected by filtration and washed with water, acetone and diethyl ether, in that order, to afford a further 12 mg of the title compound.

Nuclear Magnetic Resonance Spectrum (270 MHz, $D_2O$) δ ppm:

0.65 (3H, triplet, J=6 Hz);
0.8–1.15 (12 H, multiplet);
1.17 (3H, doublet, J=6 Hz);
1.3–1.5 (4 H, multiplet);
1.7–1.85 (2H, doublet-like);
1.95–2.1 (2H, multiplet);
2.1–2.3 (2H, multiplet);
3.20 (1H, triplet, J=3 Hz);
3.95 (1H, doublet, J=3 Hz);
5.05–5.2 (1H, multiplet).

EXAMPLE 23 cis-[trans-(l)-1,2-Diaminocyclohexane]platinum(II) {(3S, 4S)-3-[1-(R)-hydroxyethyl]-2-oxoazetidin-4-yl}carboxylate Following a procedure similar to that described in Example 16, 186 mg of the title compound were prepared from 594 mg of cis-[trans-(l)-1,2-diaminocyclohexane] platinum(II) and 218 mg of (3S, 4S)-3-[(R)-1-hydroxyethyl]-2-oxoazetidine-4-carboxylic acid (prepared as described in Preparation 3).

Nuclear Magnetic Resonance Spectrum (270 MHz, $D_2O$) δ ppm:

0.9–1.2 (4H, multiplet);
1.10 (3H, doublet, J=7 Hz);
1.3–1.5 (2H, multiplet);
1.7–2.0 (2H, multiplet);
2.1–2.3 (2H, multiplet);
3.02 (1H, doublet of doublets, J=3 & 4 Hz);
3.85 (1H, doublet, J=3 Hz);
4.04 (1H, doublet of quartets, J=4 & 7 Hz).

EXAMPLE 24 cis-[trans-(l)-1,2-Diaminocyclohexane]platinum(II) (4S)-2-oxoazetidine-4-carboxylate 735 mg of cis-[trans-(l)-1,2-diaminocyclohexane] platinum(II) dinitrate were suspended in 50 ml of water, and 230 mg of (4S)-2-oxoazetidine-4-carboxylic acid and 1.8 ml of a 1N aqueous solution of sodium hydroxide were added to the suspension, which was then stirred at 28° C. for 4 days. At the end of this time, the reaction mixture was concentrated by evaporation under reduced pressure, and then acetone was added to the residue to precipitate crystals. These crystals were collected by filtration, washed with water and with acetone and dried under reduced pressure, to give 195 mg of the title compound.

Nuclear Magnetic Resonance Spectrum (270 MHz, $D_2O$) δ ppm:

0.9–1.2 (4H, multiplet);
1.3–1.5 (2H, multiplet);
1.8–2.0 (2H, multiplet);
2.1–2.3 (2H, multiplet);
2.43 (1H, doublet of doublets, J=4.0 & 17.2 Hz);
2.52 (1H, doublet of doublets, J=6.6 & 17.2 Hz);
3.58 (1H, doublet of doublets, J=4.4 & 6.6 Hz).

EXAMPLE 25 cis-[trans-(l)-1,2-Diaminocyclohexane]platinum (II) {(3S, 4R)-3-[(R)-1-octanoyloxyethyl]-2-oxoazetidin-4-yl}acetate Following a procedure similar to that described in Example 16, 100 mg of the title compound were prepared from 579 mg of cis-[trans-(l)-1,2-diaminocyclohexane] platinum (II) dinitrate and 400 mg of [(3S, 4R)-3-(R)-1-octanoyloxyethyl)-2-oxoazetidin-4-yl]acetic acid.

Nuclear Magnetic Resonance Spectrum (270 MHz, $D_2O$) δ ppm:

0.68 (3H, triplet, J=7 Hz);
0.8–1.2 (10H, multiplet);
1.14 (3H, doublet, J=6 Hz);
1.25–1.5 (4H, multiplet);
1.7–2.0 (2H, multiplet);
2.1–2.3 (2H, multiplet);
2.40 (2H, doublet, J=7.5 Hz);
3.03 (1H, doublet of doublets, J=4 & 2);
3.86 (1H, doublet of triplets, J=2 & 7.5);
5.08 (1H, doublet of quartets, J=4).

EXAMPLE 26 cis-[trans-(l)-1,2-Diaminocyclohexane]platinum (II) (3S, 4S)-3-[(R)-1-hexanoyloxyethyl]-2-oxoazetidine-4-carboxylate Following a procedure similar to that described in Example 22, 100 mg of the title compound were prepared from 274 mg of cis-[trans-(l)-1,2-diaminocyclohexane] platinum (II) and 218 mg of (3S, 4S)-3-[(R)-1-hexanoyloxyethyl]-2-oxoazetidine-4-carboxylic acid.

Nuclear Magnetic Resonance Spectrum (270 MHz, $D_2O$) δ ppm:

0.68 (3H, triplet, J=7 Hz);
0.8–1.25 (8H, multiplet);
1.18 (3H, doublet, J=6.4 Hz);
1.3–1.5 (4H, multiplet);
1.75–1.95 (2H, multiplet);
1.95–2.05 (2H, multiplet);
2.1–2.35 (2H, multiplet);
3.21 (1H, doublet of doublets, J=3.7 & 2.5 Hz);
3.97 (1H, doublet, J=2.5 Hz);
5.13 (1H, doublet of quartets, J=3.7 & 6.4 Hz);

EXAMPLE 27 cis-[trans-(l)-1,2-Diaminocyclohexane]platinum (II) (3S, 4S)-3-[(R)-1-butanoyloxyethyl]-2-oxoazetidine-4-carboxylate Following a procedure similar to that described in Example 22, 100 mg of the title compound were prepared from 210 mg of cis-[trans-(l)-1,2-diaminocyclohexane] platinum (II) and 150 mg of (3S, 4S)-3-[(R)-1-butanoyloxyethyl]-2-oxoazetidine-4-carboxylic acid.

Nuclear Magnetic Resonance Spectrum (270 MHz, $D_2O$) δ ppm:

0.71 (3H, triplet, J=7.5 Hz);
0.85–1.15 (4H, multiplet);
1.18 (3H, doublet, J=6.6 Hz);
1.25–1.4 (2H, multiplet);
1.3–1.5 (2H, multiplet);
1.75–1.85 (2H, multiplet);
1.95–2.05 (2H, multiplet);
2.1–2.3 (2H, multiplet);
3.21 (1H, doublet of doublets, J=3.6 & 2.3 Hz);
3.96 (1H, doublet, J=2.3 Hz);
5.14 (1H, doublet of quartets, J=3.6 & 6.6 Hz).

EXAMPLE 28 cis-(cis-1,2-Diaminocyclohexane)platinum (II) (3S, 4S)-3-[(R)-1-octanoyloxyethyl]-2-oxoazetidine-4-carboxylate Following a procedure similar to that described in Example 22, 40 mg of the title compound were prepared from 300 mg of cis-(cis-1,2-diaminocyclohexane)platinum (II) dinitrate and 197 mg of (3S, 4S)-3-[(R)-1-octanoyloxyethyl]-2-oxoazetidine-4-carboxylic acid.

Nuclear Magnetic Resonance Spectrum (270 MHz, $D_2O$) δ ppm:

0.90 (3H, triplet, J=7 Hz);
1.25–1.45 (10H, multiplet);
1.39 (3H, doublet, J=6.6 Hz);
1.55–1.75 (4H, multiplet);
1.75–1.9 (4H, multiplet);
2.25–2.4 (2H, multiplet);
2.6–2.7 (2H, multiplet);
3.42 (1H, doublet of doublets, J=4.7 & 2.5 Hz);
3.99 (1H, doublet, J=2.5 Hz);
5.31 (1H, doublet of quartets, J=4.7 & 6.6 Hz).

PREPARATION 1

Sodium 2-oxoazetidine-4,4-dicarboxylate

1(a) A solution of 6.11 ml of bromoacetyl chloride in 60 ml of tetrahydrofuran was added to a solution of 24 g of diethyl N-(2,4-dimethoxybenzyl)aminomalonate in 120 ml of tetrahydrofuran, whilst ice-cooling, and then 10.3 ml of triethylamine were added dropwise to the resulting mixture. The mixture was stirred for 2 hours whilst ice-cooling, after which the precipitated crystals were filtered off, and the filtrate was concentrated by evaporation under reduced pressure. The residue was extracted with ethyl acetate, and the extract was washed with dilute hydrochloric acid, an aqueous solution of sodium bicarbonate and water, in that order. It was then freed from ethyl acetate by evaporation under reduced pressure, to give 31.5 g of an oily product. The whole of this oil was dissolved in 200 ml of benzene, and the resulting solution was mixed with 11.2 ml of triethylamine. The mixture was then stirred overnight at room temperature, after which it was diluted with ethyl acetate. The mixture was then washed with dilute aqueous hydrochloric acid, with an aqueous solution of sodium bicarbonate and with water, in that order, and the organic layer was dried over anhydrous magnesium sulfate. The solvent was then removed by distillation under reduced pressure. The residue was purified by column chromatography through 400 g of silica gel, eluted with a 1:5 by volume mixture of ethyl acetate and benzene, to afford 21 g of diethyl 1-(2,4-dimethoxybenzyl)-2-oxoazetidine-4,4-dicarboxylate.

Nuclear Magnetic Resonance Spectrum (60 MHz, $CDCl_3$) δ ppm:

1.16 (6H, triplet, J=7 Hz);
3.32 (2H, singlet);

3.78 (6H, singlet);

4.02 (4H, quartet, J=7 Hz);

4.57 (2H, singlet);

6.4 (2H, multiplet);

7.1 (1H, multiplet).

1(b) 17.4 g of diethyl 1-(2,4-dimethoxybenzyl)-2-oxoazetidine-4,4-dicarboxylate (prepared as described above) were dissolved in a mixture of 350 ml of acetonitrile and 350 ml of water. 11.2 g of potassium persulfate and 37.4 g of dibasic potassium phosphate were then added to the resulting solution, and the mixture was stirred at 65° C. for 1 hour. At the end of this time, insoluble materials were filtered off and the filtrate was freed from the solvent by evaporation under reduced pressure. The residue was extracted with ethyl acetate. The extract was washed with a saturated aqueous solution of sodium chloride, with an aqueous solution of sodium bicarbonate and with a saturated aqueous solution of sodium chloride, in that order. The solvent was then removed by distillation under reduced pressure, and the residue was purified by column chromatography through silica gel, eluted with a 1:2 by volume mixture of ethyl acetate and benzene, to give 5.72 g of diethyl 2-oxoazetidine-4,4-dicarboxylate.

Nuclear Magnetic Resonance Spectrum (60 MHz, CDCl$_3$) δ ppm:

1.28 (6H, triplet, J=7 Hz);

3.38 (2H, doublet-like, J=2 Hz);

4.26 (4H, quartet, J=7 Hz);

7.2 (1H, broad singlet).

1(c) 5.72 g of diethyl 2-oxoazetidine-4,4-dicarboxylate (prepared as described above) were dissolved in 25 ml of methanol. 53.2 ml of a 1N aqueous solution of sodium hydroxide were added to the resulting solution, and the mixture was stirred at room temperature for 1 day. At the end of this time, the reaction mixture was concentrated by evaporation under reduced pressure to give crystals, which were washed with methanol and with diethyl ether to give 5.3 g of the title compound as crystals.

PREPARATION 2

Sodium 2-oxopyrrolidine-5,5-dicarboxylate

2(a) 2.8 ml of triethylamine were added to a suspension of 2.11 g of diethyl 2-aminomalonate hydrochloride in 50 ml of methylene chloride. 1.71 g of 3-bromopropionyl chloride were then added to the mixture, whilst ice-cooling, and then the mixture was stirred for 30 minutes. At the end of this time, the reaction mixture was poured into water and extracted with diethyl ether. The extract was washed with a 5% w/v aqueous solution of sodium bicarbonate and with water, in that order, after which it was dried over anhydrous magnesium sulfate. The solvent was then removed by distillation under reduced pressure, to give 2.5 g of diethyl 2-(3-bromopropionamido)malonate.

Nuclear Magnetic Resonance Spectrum (60 MHz, CDCl$_3$) δ ppm:

1.28 (6H, triplet, J=7.0 Hz);

2.87 (2H, triplet, J=6.6 Hz);

3.61 (2H, triplet, J=6.5 Hz);

4.25 (4H, quartet, t=7.0 Hz);

5.14 (1H, doublet, J=7.0 Hz);

6.65 (1H, broad singlet).

2(b) 314 μl of 1,8-diaza[5.4.0]-7-undecene were added to a solution of 620 mg of diethyl 2-(3-bromopropionamido) malonate (prepared as described above) dissolved in methylene chloride, and the mixture was stirred at room temperature for 3 hours. At the end of this time, the reaction mixture was concentrated by evaporation under reduced pressure, poured into water and then extracted with diethyl ether. The extract was washed with 5% w/v aqueous hydrochloric acid, with a 5% w/v aqueous solution of sodium bicarbonate and with water, in that order, and dried over anhydrous magnesium sulfate. The solvent was then removed by distillation under reduced pressure, to give a crude product. This was purified by column chromatography through silica gel, eluted with a 2:1 by volume mixture of cyclohexane and ethyl acetate, to give 171 mg of diethyl 2-oxopyrrolidine-5,5-dicarboxylate.

Nuclear Magnetic Resonance Spectrum (60 MHz, CDCl$_3$) δ ppm:

1.28 (6H, triplet, J=7.0 Hz);

2.2–2.8 (4H, multiplet);

4.25 (4H, quartet, J=7.0 Hz);

7.5 (1H, broad singlet).

2(c) 8.74 ml of a 1N aqueous solution of sodium hydroxide were added to a solution of 1.0 g of diethyl 2-oxopyrrolidine-5,5-dicarboxylate (prepared as described above) in 10 ml of ethanol, and the mixture was stirred at room temperature for 3 days. At the end of this time, the solvent was removed by distillation under reduced pressure, and the residual crystals were washed with acetone and dried to give 950 mg of sodium 2-oxopyrrolidine-5,5-dicarboxylate as a colorless powder.

Nuclear Magnetic Resonance Spectrum (60 MHz, D$_2$O) δ ppm: 2.35 (broad singlet).

Infrared Absorption Spectrum (KBr) $v_{max}$ cm$^{-1}$: 3180, 1700, 1630.

PREPARATION 3

3-[(R)-1-Hydroxyethyl]-2-oxoazetidine-4-carboxylic Acid

3(a) 14 g of benzyl 1-(2,4-dimethoxybenzyl)-3-[(R)-1-hydroxyethyl]-2-oxoazetidine-4-carboxylate [which had been synthesized according to a procedure similar to that described in Tetrahedron 46, 1795 (1984)] were dissolved in a mixture of 420 ml of acetonitrile and 420 ml of water. 66.1 g of potassium persulfate and 23.3 g of dibasic potassium phosphate were added to the solution, and the mixture was stirred at 70° C. for 60 minutes. At the end of this time, insoluble materials were filtered off, and the filtrate was concentrated by evaporation under reduced pressure. The residue was extracted with ethyl acetate. The extract was washed with a saturated aqueous solution of sodium chloride, dried over anhydrous magnesium sulfate and freed from the solvent by evaporation under reduced pressure. The residue was purified by column chromatography through silica gel to afford 6.1 g of benzyl 3-[(R)-1-hydroxyethyl]-2-oxoazetidine-4-carboxylate.

Nuclear Magnetic Resonance Spectrum (60 MHz, CDCl$_3$) δ ppm:

1.26 (3H, doublet, J=6.0 Hz);

3.19–3.45 (2H, multiplet);

3.93–4.49 (1H, multiplet);

4.30 (1H, doublet, J=3.0 Hz);

5.17 (2H, singlet);

6.88 (1H, singlet);

7.33 (5H, singlet).

3(b) 500 mg of the benzyl 3-[(R)-1-hydroxyethyl]-2-oxoazetidine-4-carboxylate (prepared as described in above)

were dissolved in 5 ml of methanol, and the mixture was hydrogenated in the presence of 100 mg of a 10% w/w palladium-on-carbon catalyst at room temperature for 2 hours. At the end of this time, the catalyst was removed by filtration. The filtrate was concentrated by evaporation under reduced pressure, to give 310 mg of the title compound as a colorless oil.

Nuclear Magnetic Resonance Spectrum (60 MHz, $CD_3OD$) δ ppm:

1.27 (3H, doublet, J=6.0 Hz);
3.2–3.4 (1H, multiplet);
4.23 (1H, doublet, J=3.0 Hz);
4.0–4.35 (1H, multiplet);
8.07 (1H, broad singlet).

EXPERIMENT

In the following experiment, the test animals used were 8 to 9 week old female mice of the $CDF_1$ strain, each weighing 20–25 g. The standard L1210 leukemia cells were supplied by Dr. T. Yamamoto of the Institute of Medical Science, University of Tokyo, Japan.

$CDF_1$ mice were inoculated intraperitoneally with L1210 cells ($10^5$ cells/mouse). The test compound is as identified in the following Table 6. In the case of the compounds of the present invention and carboplatin, this was dissolved in 5% v/v aqueous mannitol, whilst cisplatin was dissolved in a 5% v/v solution of mannitol in physiological saline. Each drug was injected intraperitoneally on days 1 and 4 following tumor implantation. The number of mice in each test group was 6.

The increase in life span (ILS) was calculated as follows:

$$ILS\% = [(S_t/S_u) - 1] \times 100$$

in which:

$S_t$=weighted median number of days survival of treated mice; and $S_u$=weighted median number of days survival of untreated mice.

The results are shown in Table 6.

TABLE 6

| Compound | Dose (mg/kg) | Wt. Change (g) 1) | ILS (%) 2) | Survivors on day 42 |
|---|---|---|---|---|
| Untreated Control | — | +1.9 | — | 0/6 |
| Compound of Example 1 | 10 | +1.0 | >196 | 4/6 |
| | 20 | −0.2 | >198 | 6/6 |
| | 40 | −0.2 | >196 | 4/6 |
| | 80 | −1.2 | >197 | 5/6 |
| Compound of Example 14 | 2.5 | −0.3 | >230 | 5/6 |
| | 5 | −0.3 | >231 | 6/6 |
| | 10 | −1.5 | >231 | 6/6 |
| | 20 | −5.5 | 40 | 0/6 |
| carboplatin | 5 | +1.3 | 7 | 0/6 |
| | 10 | +2.0 | 7 | 0/6 |
| | 20 | +0.8 | 7 | 0/6 |
| | 40 | +0.4 | 10 | 0/6 |
| | 80 | −0.5 | 23 | 0/6 |
| cisplatin | 1.25 | +2.7 | 19 | 0/6 |
| | 2.5 | +0.7 | 82 | 0/6 |
| | 5 | −2.2 | 254 | 3/6 |

Notes:
1) Change in body weight from day 1 to day 7.
2) Increase in life span.

We claim:

1. A compound selected from the group consisting of:
   1,2-diaminocyclohexaneplatinum(II) 3-[1-(methoxymethoxy)ethyl]-2-oxoazetidin-4-ylacetate;
   1,2-diaminocyclohexaneplatinum(II) 3-[1-(2-methoxyethoxymethoxy)ethyl]-2-oxoazetidin-4-ylacetate;
   1,2-diaminocyclohexaneplatinum(II) 3-(1-octanoyloxyethyl)-2-oxoazetidin-4-ylcarboxylate;
   1,2-diaminocyclohexaneplatinum(II) 3-(1-t-butyldimethylsilyloxyethyl)-2-oxoazetidin-4-ylcarboxylate;
   cis-[trans-(l)-1,2-diaminocyclohexane]platinum(II) {(3S, 4R)-3-[(R)-1-(methoxymethoxy)ethyl]-2-oxoazetidin-4-yl}acetate;
   cis-[trans-(l)-1,2-diaminocyclohexane]platinum(II) {(3S, 4R)-3-[(R)-1-(2-methoxyethoxymethoxy)ethyl]-2-oxoazetidin-4-yl}acetate;
   cis-[trans-(l)-1,2-diaminocyclohexane]platinum(II) {(3S, 4S)-3-[(R)-1-octanoyloxyethyl]-2-oxoazetidin-4-yl}carboxylate; and
   cis-[trans-(l)-1,2-diaminocyclohexane]platinum(II) {(3S, 4S)-3-[(R)-1-t-butyldimethylsilyloxyethyl]-2-oxoazetidin-4-yl}carboxylate.

2. A composition comprising an anti-tumor agent and a pharmaceutically acceptable carrier or diluent, wherein said anti-tumor agent is selected from the group consisting of:
   1,2-diaminocyclohexaneplatinum(II) 3-[1-(methoxymethoxy)ethyl]-2-oxoazetidin-4-ylacetate;
   1,2-diaminocyclohexaneplatinum(II) 3-[1-(2-methoxyethoxymethoxy)ethyl]-2-oxoazetidin-4-ylacetate;
   1,2-diaminocyclohexaneplatinum(II) 3-(1-octanoyloxyethyl)-2-oxoazetidin-4-ylcarboxylate; and
   1,2-diaminocyclohexaneplatinum(II) 3-(1-t-butyldimethylsilyloxyethyl)-2-oxoazetidin-4-ylcarboxylate.

3. A composition comprising an anti-tumor agent and a pharmaceutically acceptable carrier or diluent, wherein said anti-tumor agent is selected from the group consisting of:
   cis-[trans-(l)-1,2-diaminocyclohexane]platinum(II) {(3S, 4R)-3-[(R)-1-(methoxymethoxy)ethyl]-2-oxoazetidin-4-yl}acetate;
   cis-[trans-(l)-1,2-diaminocyclohexane]platinum(II) {(3S, 4R)-3-[(R)-1-(2-methoxyethoxymethoxy)ethyl]-2-oxoazetidin-4-yl}acetate;
   cis-[trans-(l)-1,2-diaminocyclohexane]platinum(II) {(3S, 4S)-3-[(R)-1-octanoyloxyethyl]-2-oxoazetidin-4-yl}carboxylate; and
   cis-[trans-(l)-1,2-diaminocyclohexane]platinum(II) {(3S, 4S)-3-[(R)-1-t-butyldimethylsilyloxyethyl]-2-oxoazetidin-4-yl}carboxylate.

4. The compound of claim 1, which is 1,2-diaminocyclohexaneplatinum(II) 3-[1-(methoxymethoxy)ethyl]-2-oxoazetidin-4-ylacetate.

5. The compound of claim 1 which is cis-[trans-(l)-1,2-diaminocyclohexane]platinum(II) {(3S, 4S)-3-[(R)-1-(methoxymethoxy)ethyl]-2-oxoazetidin-4-yl}acetate.

6. The compound of claim 1, which is 1,2-diaminocyclohexaneplatinum(II) 3-[1-(2-methoxyethoxymethoxy)ethyl]-2-oxoazetidin-4-ylacetate.

7. The compound of claim 1, which is cis-[trans-(l)-1,2-diaminocyclohexane]platinum(II) {(3S, 4R)-3-[(R)-1-(2-methoxyethoxymethoxy)ethyl]-2-oxoazetidin-4-yl}acetate.

8. The compound of claim 1, which is 1,2-diaminocyclohexaneplatinum(II) 3-(1-octanoyloxyethyl)-2-oxoazetidin-4-ylcarboxylate.

9. The compound of claim 1, which is cis-[trans-(l)-1,2-diaminocyclohexane]platinum(II) {(3S, 4S)-3-[(R)-1-octanoyloxyethyl]-2-oxoazetidin-4-yl}carboxylate.

10. The compound of claim 1, which is 1,2-diaminocyclohexaneplatinum(II) 3-(1-t-butyldimethylsilyloxyethyl)-2-oxoazetidin-4-ylcarboxylate.

11. The compound of claim 1, which is cis-[trans-(l)-1,2-diaminocyclohexane]platinum(II) {(3S, 4S)-3-[(R)-1-t-butyldimethylsilyloxyethyl]-2-oxoazetidin-4-yl}carboxylate.

* * * * *